(12) United States Patent
Bomshteyn et al.

(10) Patent No.: US 6,890,533 B2
(45) Date of Patent: May 10, 2005

(54) BETULINOL DERIVATIVES

(75) Inventors: Arkadiy L. Bomshteyn, Brooklyn, NY (US); Premila Rathnam, Englewood Cliffs, NJ (US); Brij B. Saxena, Englewood, NJ (US)

(73) Assignee: Cornell Research Foundation, Inc., Ithaca, NY (US)

( * ) Notice: Subject to any disclaimer, the term of this patent is extended or adjusted under 35 U.S.C. 154(b) by 312 days.

(21) Appl. No.: 09/089,894

(22) Filed: Jun. 3, 1998

(65) Prior Publication Data

US 2004/0001837 A1 Jan. 1, 2004

Related U.S. Application Data

(60) Provisional application No. 60/048,621, filed on Jun. 4, 1997.

(51) Int. Cl.$^7$ .............................................. A61K 39/00
(52) U.S. Cl. ................. 424/179.1; 552/500; 424/178.1; 424/193.1; 514/2; 514/345; 514/387.1
(58) Field of Search ...................... 552/500; 424/178.1, 424/193.1, 179.1; 514/2, 345, 387.1; 530/345, 387.1

(56) References Cited

U.S. PATENT DOCUMENTS

| | | | |
|---|---|---|---|
| 4,122,166 A | 10/1978 | Tribble et al. | |
| 4,146,615 A | 3/1979 | Fauran et al. | |
| 4,671,958 A | 6/1987 | Rodwell et al. | |
| 4,749,567 A | 6/1988 | McNatty et al. | |
| 4,801,688 A | 1/1989 | Laguzza et al. | |
| 5,013,547 A | 5/1991 | Sweet et al. | |
| 5,034,223 A | 7/1991 | Abrams et al. | 424/85.8 |
| 5,064,823 A | 11/1991 | Lee et al. | |
| 5,144,010 A | 9/1992 | Erlanger et al. | |
| 5,162,218 A | 11/1992 | Schultz | |
| 5,166,319 A | 11/1992 | Wrasidlo | |
| 5,272,253 A | 12/1993 | Koppel et al. | 530/332 |
| 5,328,840 A | 7/1994 | Coller | 435/240.2 |
| 5,399,672 A | 3/1995 | Jalalian et al. | 530/403 |
| 5,468,888 A | 11/1995 | Bouboutou et al. | 554/58 |
| 5,639,656 A | 6/1997 | Wright, Jr. | 435/344.1 |
| 5,643,884 A | * 7/1997 | Anderson | 514/26 |
| 5,679,828 A | * 10/1997 | Lee | 560/116 |

OTHER PUBLICATIONS

Bejar, Int. J. Pharmacogn. 33, 25–32, 1995.*
Kochergina, Chem. Abstr. 106, 153022, 1987.*
Pokhilo, Chem. Abstr. 114, 98300, 1991.*
Pisha, Nature Medicine 1 (10) 1046–51, 1995.*
Macias, Phytochemistry 36, 1369–79, 1994.*
Kircher, Phytochemistry 19, 2707–12, 1980.*
House, "Modern Synthetic Reactions", 2$^{nd}$ Ed (W.A. Benjamin, Inc.) pp. 257–265 1972.*
The Merck Index, 11th Edition, entry 1212, p. 185 (betulin) 1989.*
Sheth et al., "Tumor–Inhibitory Agent from *Hyptis emoryi* (Labiatae)," *Journal of Pharmaceutical Sciences*, 61:1819 (1972).

Sheth et al., "Antitumor Agents from *Alnus oregona* (Betulaceae)," *Journal of Pharmaceutical Sciences*, 62:139–140 (1973).

Ukkonen et al., "Birch Bark Extractives," *Kemia Kemi*, 6:217–220 (1979).

Tomas et al., "A Cytotoxic Triterpenoid and Flavonoids from *Crossopteryx febrifuga*," *Planta Medica*, 54:266–267 (1988).

"Bark of Common Northern Birch Tree May Be Invaluable As a New Treatment for Melanoma," *The Medical Herald*, pp. 4–5 (May 1995).

Lindgren et al., "Lupan–3β, 20 diol and Lupan–3β, 28–triol in Bank from Birch, *Betula verrucosa* Erh.," *Acta Chem. Scand.*, 20:1720–1721 (1966).

Jaaskelainen, "Betulinol and Its Utilisation," *Papperi Ha Puu–Papper Orc Trä.*, 63:599–603 (1981).

Rathnam et al., "Daunorubicin Conjugates of Antibodies to CA–125 and Lutropin Receptor," FASEB Journal, Experimental Biology 96, Washington, D.C. (Apr. 14–17, 1996) (abstract).

(Continued)

*Primary Examiner*—Robert A. Wax
*Assistant Examiner*—David Lukton
(74) *Attorney, Agent, or Firm*—Nixon Peabody LLP

(57) ABSTRACT

The present invention is directed to betulinol derivatives and betulinol-antibody conjugates having the formulae:

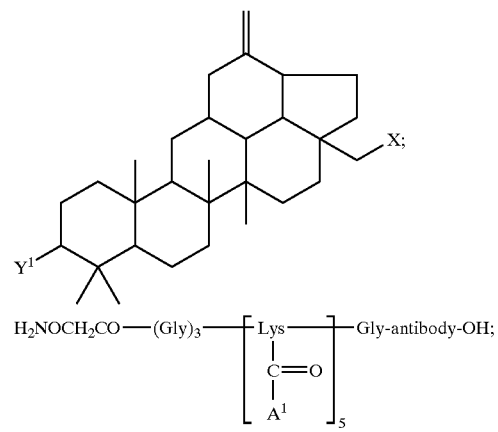

and

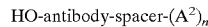

and, in particular, betulinol dimethyl ether. Methods for making and using these derivatives and conjugates, as well as a method for making and using betulonic aldehyde, are also disclosed.

46 Claims, 1 Drawing Sheet

OTHER PUBLICATIONS

Suwa et al., "Epidermal Growth Factor Receptor–Dependent Cytotoxic Effect of Anti–EGFR Antibody–Ribonuclease Conjugate on Human Cancer Calls," *Anticancer Research* 19:4161–4166 (1999).

Takahashi et al., "Experimental Treatment of Malignant Gliomas with Human Monoclonal Antibody–Drug Conjugates," *Anticancer Research* 19:4151–4156 (1999).

Charles et al., "Atrophy of Cholinergic Basal Forebrain Neurons Following Excitotoxic Cortical Lesions is Reversed by Intravenous Administration of an NGF Conjugate," *Brain Research* 728:193–203 (1996).

Roy et al., "Targeting T Cells Against Brain Tumors with a Bispecific Ligand–Antibody Conjugate," *Int. J. Cancer* 76:761–766 (1998).

Harapanhalli et al., "Lysine–Directed Conjugation of Ethidium Homodimer to B72.3 Antibody: Retention of Immunoreactivity but Altered Tumor Targeting," *Nuclear Medicine & Biology* 25:267–278 (1998).

Crosasso et al., "Antitumoral Activity of Liposomes and Immunoliposomes Containing 5–Fluorouridine Prodrugs," *Journal of Pharmaceutical Sciences* 86:832–839 (1997).

Cheng, "Bystander Killing of Tumour Cells by Antibody–Targeted Enzymatic Activation of a Glucuronide Prodrug," *British Journal of Cancer* 79:1378–1385 (1999).

Chang et al., "Five Different Anti–Prostate–specific Membrane Antigen (PSMA) Antibodies Confirm PSMA Expression in Tumor–Associated Neovasculature," *Cancer Research* 59:3192–3198 (1999).

Oosterwijk et al., "Antibody Localization in Human Renal Cell Carcinoma: A Phase I Study of Monocolonal Antibody G250," *Journal of Clinical Oncology* 11:738–750 (1993).

Texter et al., "The Role of Monoclonal Antibody in the Management of Prostate Adenocarcinoma," *The Journal of Urology* 160:2393–2395 (1998).

Kaminski et al., "Radioimmunotherapy of B–Cell Lymphoma With [$^{131}$I]Antigen–B1 (Anti–CD20) Antibody," *The New England Journal of Medicine* 329:459–465 (1993).

Houba et al., "Improved Characteristics of a Human β–Glucuronidase–Antibody Conjugate After Deglyconsylation for Use in Antibody–Directed Enzyme Prodrug," *Bioconjugate Chem.*, 7:606–611 (1996).

Wolfe et al., "Antibody–Directed Enzyme Prodrug Therapy With the T268G Mutant of Human Carboxypeptidase A1: In Vitro Studies With Prodrugs of Methotrexate and the Thymidylate Synthase Inhibitors GW1031 and GW1843," *Bioconjugate Chem.*, 10:38–48 (1999).

Somasundaram et al., "Development of a Trispecific Antibody Conjugate Directs Two Distinct Tumor–Associated Antigens to CD64 on Myeloid Effector Cells," *Human Antibodies*, 9:47–54 (1999).

Nathan et al., "Hydrogels Based on Water–Soluble Poly(ether urethanes) Derived from L–Lysine and Poly(ethylene glycol)," *Macromolecules*, 25:4476–4484 (1992).

Nathan et al., "Copolymers of Lysine and Polyethylene Glycol: A New Family of Functionalized Drug Carriers," *Bioconjugate Chem.*, 4:54–62 (1993).

Poiani et al., "Conjugates of cis–4–Hydroxy–L–proline and Poly(PEG–Lys), a Water Soluble Poly(ether urethane): Synthesis and Evaluation of Antifibrotic Effects in Vitro and in Vivo," *Bioconjugate Chem.*, 5:621–630 (1994).

Vilaseca et al., "Protein Conjugates of Defined Structure: Synthesis and Use of a New Carrier Molecule," *Bioconjugate Chem.*, 4:515–520 (1993).

Haselgrübler et al., "Synthesis and Applications of a New Poly(ethylene glycol) Derivative for the Crosslinking of Amines With Thiols," *Bioconjugate Chem.*, 6:242–248 (1995).

Senter et al., "Poly(ethylene glycol)–Doxorubicin Conjugates Containing β–Lactamase–Sensitive Linkers," *Bioconjugate Chem.*, 6:389–394 (1995).

Sejbal et al., "Functionalization of Lupane with Chromium (VI) Oxide, a Remark on the Structure of Clerodone," *Collect. Czech. Chem. Commun.* 61:1371–1379 (1996).

Pouzar et al., "Reduction and Steric Interaction of 12–Lupanone Derivatives," *Collection Czechoslov. Chem. Commun.* 41:3452–3466 (1976).

Simonsen et al., "The Triterpenes and Their Derivatives," *The Terpenes*, vol. 4, Ch. II, Alcohols, Cambridge University Press, pp. 287–369 (1957).

* cited by examiner

BETULINOL DERIVATIVES

The present application claims the benefit of U.S. Provisional Patent Application Serial No. 60/048,621, filed Jun. 4, 1997, which is hereby incorporated by reference.

FIELD OF THE INVENTION

The present invention relates generally to betulinol derivatives and, in particular, to betulinol-antibody conjugates and to methods for making and using these betulinol derivatives and betulinol-antibody conjugates.

BACKGROUND OF THE INVENTION

Betulinol is one of the more plentiful triterpenes, constituting up to 24 per cent of the outer bark of the white birch (*Betula alba*) and as much as 35 per cent of the outer bark and about 5 per cent of the inner bark of the Manchurian white birch (*Betula platyphylla*) (Hirota et al., *J.S.C.I. Japan*, 47:922 (1944)). It also occurs in the free state in the barks of the following trees: the yellow and black birch (Steiner, *Mikrochemie, Molisch-Festschrift*, p. 405 (1936)), *Corylus avellana, Carpinus betulus* (Feinberg et al., *Monatsh*, 44:261 (1924); Brunner et al., *Monatsh*, 63:368 (1934); and Brunner et al., *Monatsh*, 64:21 (1934)), and *Lophopetalum toxicum* (Dieterle et al., *Arch. Pharm.*, 271:264 (1933)). The exudate from the bark of *Trochodendron aralioides*, which constitutes Japanese bird-lime, contains betulin palmitate (Shishido et al., *J.S.C.I. Japan*, 45:436 (1942)). Betulin has also been isolated from rosehips (Zimmermann, *Helv. Chim. Acta*, 27:332 (1944)) and from the seeds of *Zizyphus vulgaris* Lamarck var. *spinosus* Bunge (Rhamnaceae) (Kawaguti et al., *J. Pharm. Soc. Japan*, 60:343 (1940)). Ruhemann et al., *Brennstoff-Ch.*, 13:341 (1932) discloses the presence of betulin, allobetulin, and an "oxyallobetulin" in the saponifiable portion of a benzene-alcohol extract of mid-German brown coal. In addition, the following group of lupon-row derivatives from the birch cortex extract have been identified: (a) betulinol, (b) betulinic acid, (c) betulin aldehyde, (d) betulonic acid, and (e) betulon aldehyde (Rimpler et al., *Arch. Pharm. Und. Ber. Dtsh. Ppharmaz Jes*, 299:422–428 (1995); Lindgren et al., *Acta Chem.*, 20:720 (1966); and Jaaskelainen, *P. Papperi Ja Puu-Papper Och Tra.*, 63:599–603 (1989)).

Birch tree cortex-extracted betulinol was first mentioned as an antiseptic in 1899. Subsequently, compounds singled out from extracts of *Hyptis emory* and *Alnus oregonu*, identified as pentacyclic styrenes and their derivatives, were shown to inhibit carcinosarcoma growth (Sheth et al., *J. Pharm. Sci.*, 61:1819 (1972) and Sheth et al., *J. Pharm. Sci.*, 62:139–140 (1973)). It has been suggested that betulinic acid is the main anti-tumor agent in the mixture of terpenoids (Tomas et al., *Planta Medicina*, 54:266–267 (1988) and Ahmat et al., *J. Indian Chem. Soc.*, 61:92–93 (1964)). In particular betulinic acid showed cytotoxic activity against carcinoma cell line CO-115 of the large intestine (LD 50=0.375 mg/ml) (Ukkonen et al., *Birch bark extractive kemia kemi*, 6:217 (1979)).

The use of chemotherapeutic agents in the treatment of a variety of cancers has become a well established part of cancer treatment regimens, especially where the disease has progressed to an advanced stage. However, these chemotherapeutic agents act not only on malignant cells but have adverse effects on non-target cells as well, particularly on the rapidly proliferating cells of the gastrointestinal tract and bone marrow. When employed in the high concentrations frequently required to be effective in killing cancer cells, these cytotoxic drugs give rise to undesirable and frequently severe side effects. Although the concept of site-directed chemotherapy is quite old, only a small number of antineoplastic drugs and toxins have been successfully coupled to monoclonal and polyclonal antibodies.

Therefore, a need continues to exist for chemotherapeutic agents and, in particular, for site-directed chemotherapeutic agents. The present invention is directed to meeting this need.

SUMMARY OF THE INVENTION

The present invention relates to a diether having the formula:

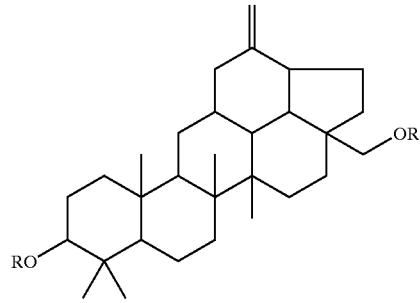

wherein R is an alkyl group.

The present invention also relates to a method for preparing the diether. The method includes alkylating a dialcohol having the formula:

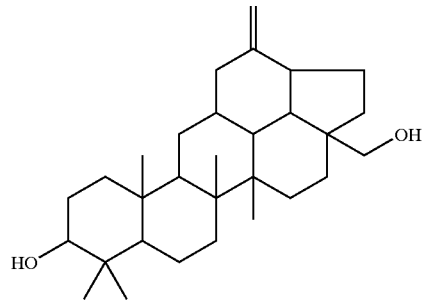

with a nitrile having the formula:

R—C≡N under conditions effective to form the diether.

In another aspect, the present invention further relates to a method of preparing betulonic aldehyde. The method includes oxidizing betulinol with chromium anhydride in acetone in the presence of sulfuric acid under conditions effective to produce betulonic aldehyde.

In still another aspect, the present invention relates to a compound having the formula:

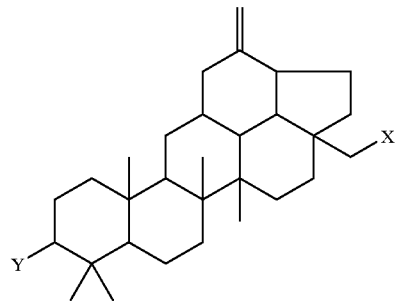

wherein
X or Y is a -peptide-Q moiety and the other of X and Y is a hydroxy group, an alkoxy group, an alkanoyloxy group, or a -peptide-Q moiety;

Q is a hydroxy group, a —NHNH$_2$ moiety, an —NHNH—C(O)CH$_2$Hal moiety, an -antibody-OH moiety, or an —NHNH—C(O)-antibody-OH moiety; and Hal is a halogen.

The present invention is also related to a method of producing a betulinol-antibody conjugate having the formula:

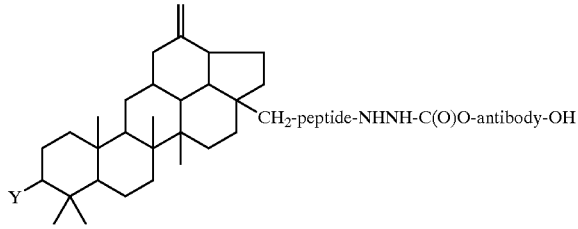

wherein

Y is a hydroxy group, an alkoxy group, or an alkanoyloxy group

The method includes converting a haloacetylhydrazide having the formula:

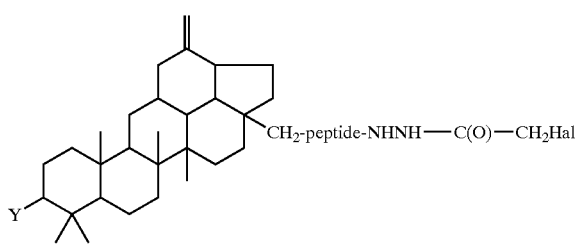

wherein

Hal is a halogen with an antibody having the formula H-antibody-OH under conditions effective to produce the betulinol-antibody conjugate.

The present invention, in yet another aspect thereof, relates to a betulinol-antibody conjugate having the formula:

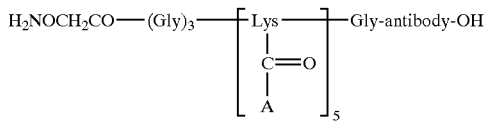

wherein

A are independently selected from the group consisting of a —CHO moiety and a moiety having the formula:

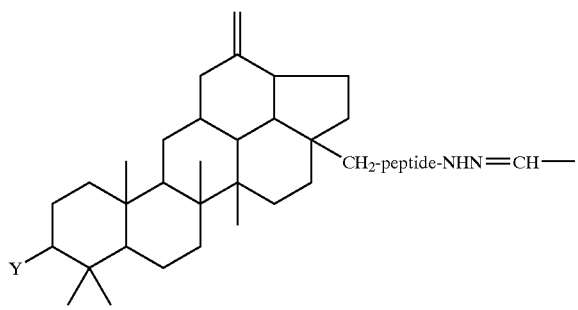

provided that at least one of A is not —CHO; and

Y is a hydroxy group, an alkoxy group, or an alkanoyloxy group.

The present invention also relates to a method of producing the betulinol-antibody conjugate described in the preceding paragraph. The method includes converting a carrier molecule having the formula:

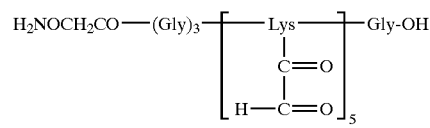

with a hydrazide having the formula:

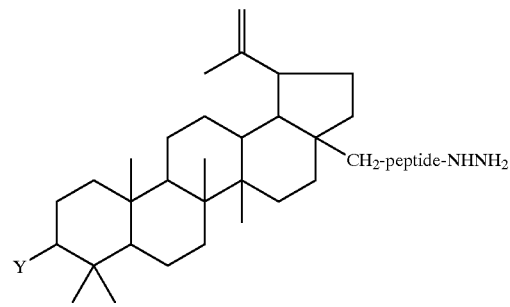

and an antibody having the formula H-antibody-OH under conditions effective to produce the betulinol-antibody conjugate.

In yet another aspect, the present invention relates to a betulinol-antibody conjugate having the formula:

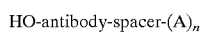

wherein

A is a moiety having the formula:

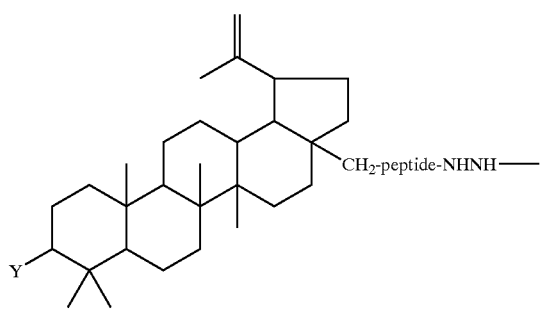

Y is a hydroxy group, an alkoxy group, or an alkanoyloxy group; and n is an integer from 1 to 100.

The present invention also relates to a method of producing the betulinol-antibody conjugate described in the preceding paragraph. A crosslinker having a first reactive terminus and one or more second reactive termini is provided. An antibody is reacted with the first reactive terminus, and a hydrazide having the formula:

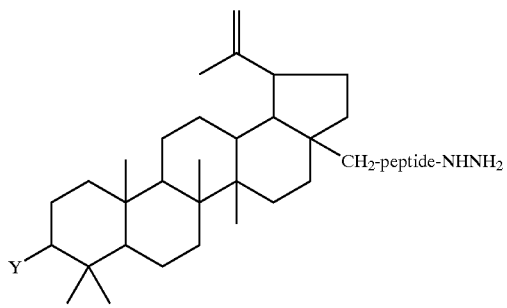

is reacted with one or more of the one or more second reactive termini under conditions effective to produce the betulinol-antibody conjugate.

The compounds, diethers, and betulinol-antibody conjugates of the present invention can be used to treat patients suffering from cancer.

More particularly, in yet another aspect thereof, the present invention relates to method of treating cancer. The method includes administering to a cancer patient an effective amount of a compound. The compound is selected from the group consisting of betulonic aldehyde and compounds having the formulae:

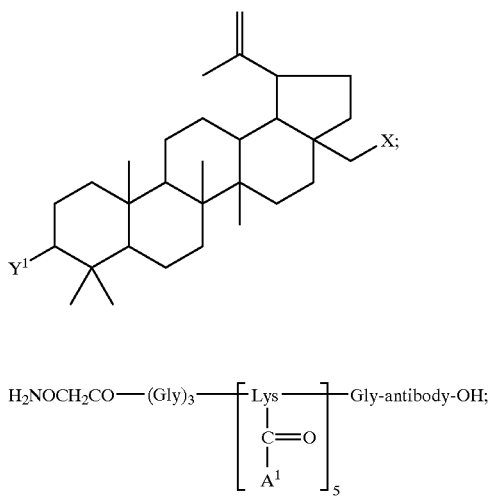

and

HO-antibody-spacer-$(A^2)_n$ wherein $A^1$ is a moiety having the formula:

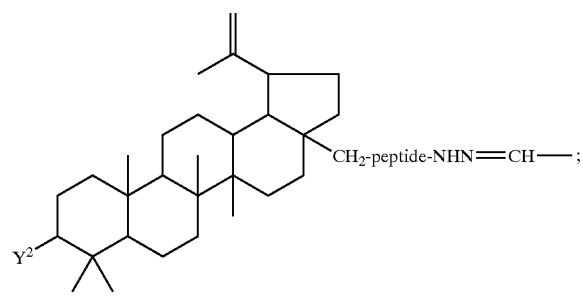

$A^2$ is a moiety having the formula:

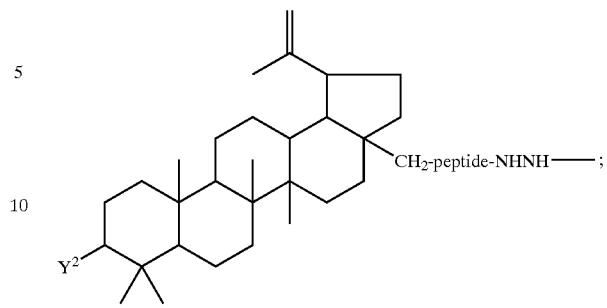

n is an integer from 1 to 100;

X and $Y^1$ are each independently selected from the group consisting of a hydroxy group, an alkoxy group, an alkanoyloxy group, and a-peptide-NHNH—C(O)-antibody-OH moiety;

$Y^2$ is selected from the group consisting of a hydroxy group, an alkoxy group, and an alkanoyloxy group; and HO-antibody-H is an antibody targeted to a site to be treated in the patient.

DETAILED DESCRIPTION OF THE INVENTION

Figure 1:
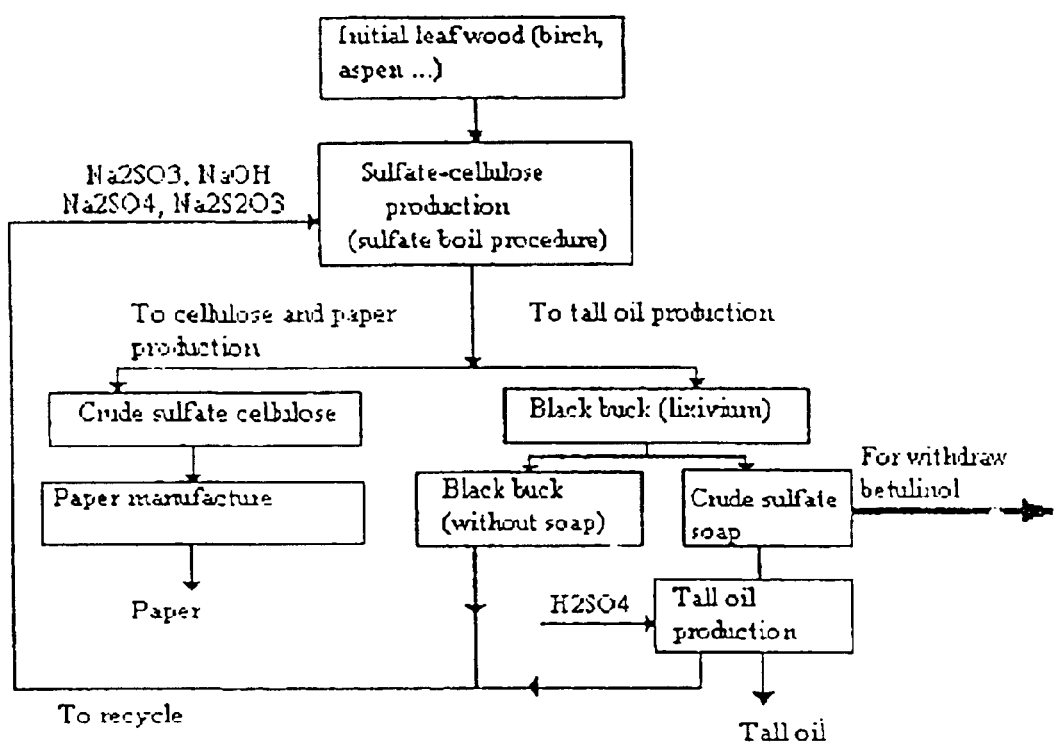
FIG. 1 is a schematic flow diagram depicting a process for producing betulinol.

The present invention relates to a diether having the formula:

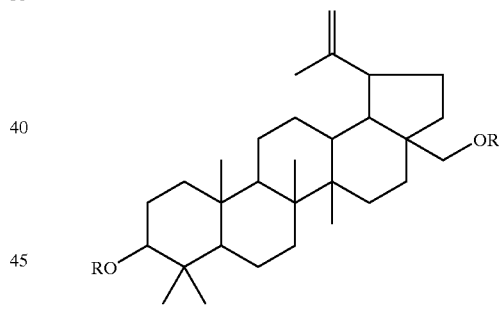

R is an alkyl group. R can be an unsubstituted alkyl, or it can be substituted with any number and combination of known substituents, such as sulfo, carboxy, cyano, halogen (e.g., fluoro, chloro), hydroxyl, alkenyl (e.g., allyl, 2-carboxy-allyl), alkoxy (e.g., methoxy, ethoxy), aryl (e.g., phenyl, p-sulfophenyl), aryloxy (e.g., phenyloxy), carboxylate (e.g., methoxycarbonyl, ethoxycarbonyl), acyloxy (e.g., acetyloxy), acyl (e.g., acetyl, propionyl), amino (including unsubstituted-monosubstituted-, and disubstituted-amino as well as cyclic amino groups (such as piperidino and morpholino) and the like. The alkyl group can be linear, branched, or cyclic. Illustrative examples of suitable alkyl groups include, methyl, ethyl, n-propyl, isopropyl, n-butyl, isobutyl, tert-butyl, n-pentyl, neopentyl, cyclopentyl, n-hexyl, and cyclohexyl. Preferably R is methyl, in which case the diether is betulinol dimethyl ether (also designated as "cornelon").

The diether of the present invention has a number of optically active carbon atoms. It is preferred that the diether be optically pure, and it is yet more preferred that each of the chiral centers in the diether have the conformation of that of naturally occurring betulinol as shown in the formula below:

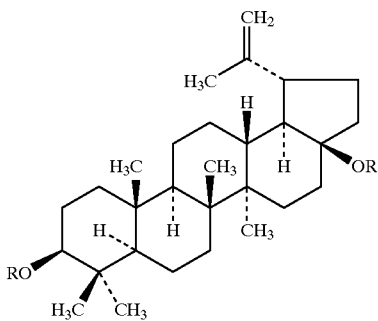

The diether can be prepared in a variety of ways. One particularly preferred preparative method, a method to which the present invention also relates, includes alkylating a dialcohol having the formula:

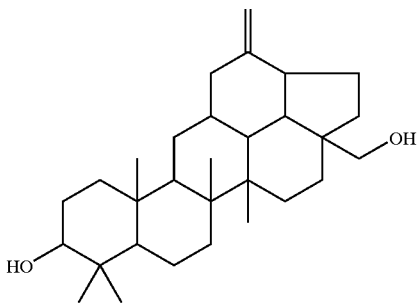

with a nitrile having the formula:

The dialcohol starting material for this reaction can be betulinol, such as betulinol isolated from natural products. Methods for isolating betulinol from a variety of sources are well known. For example, betulinol can be isolated from the outer layer of the bark of the white birch tree *Betula alba* by sublimation (Lowitz, *Crell's Annalen*, 1:312 (1788) and Mason, *Silliman's Am. J.*, 20:282 (1831), which are hereby incorporated by reference) or by extraction with an alcohol, such as ethanol (Hunefeld, *J. Prakt. Chem.*, 7:53 (1836) and Hess, *Poggendorff's Annalen*, 46:319 (1839), which are hereby incorporated by reference). Other sources of betulinol and methods for its isolation and purification have been described in, for example, Sheth et al., *J. Pharm. Sci.*, 61:1819 (1972) (raw vegetables and extracts of *Hyptis emory*) and Sheth et al., *J. Pharm. Sci.*, 62:139–140 (1973) (*Alnus oregonu*), which are hereby incorporated by reference.

In a preferred method, betulinol is isolated from the non-saponifiable substance of floral soap, such as, for example, by the method depicted in FIG. 1. Briefly, the crushed initial leaf wood and components of a sulfate boiling procedure (NaOH, $Na_2SO_4$, $Na_2S_2O_3$, $Na_2SO_3$) are lodged to a boiling pot in a batch or continuous process. Under the temperature of 110° C. to 120° C. and, optionally, at increased pressure, lignin (the component of wood) dissolves. Crude cellulose is derived from the pulping liquor which is composed of lignin, cellulose, and black buck. Black buck is a composition of black buck with salts of tall acid and non-saponifiable substances. The crude cellulose is used in paper production, whereas the sulfate soap is separated from the black buck by centrifugation or by a settling process. Treatment of the sulfate soap with sulfuric acid produces tall oil. The non-saponifiable substances are separated as crude betulinol. Recrystallization of the crude betulinol, such as from acetone, ethyl acetate, isopropanol, butanol, ethanol, and the like, yields pure betulinol. The black buck residue present after centrifugation or settling can be advantageously recycled as shown in FIG. 1.

Although the purity of the betulinol used as the starting material in the synthesis of the diether is not critical to the practice of the present invention, it is preferred that betulinol having a purity of at least 92–94% and a melting point of 241–243° C. be used. Betulinol having these properties can be obtained using the preferred isolation and purification methods described above.

Once the dialcohol is provided, it is alkylated with a nitrile having the formula R—C≡N. The identity of the nitrile used depends on the identity of the R groups desired in the diether. For example, where betulinol dimethyl ether is desired, the nitrile is acetonitrile. Other nitriles suitable for use in preparing other diethers include propionyl nitrile, butyryl nitrile, pentanoyl nitrile, hexanoyl nitrile, benzylacetonitrile, and the like. Preferably the dialcohol and nitrile are present in at least a 1:2 molar ratio, more preferably, in a molar ratio of from about 1:20 to 1:60, and, most preferably, in a molar ratio of about 1:40. The reaction can be carried out without the use of a solvent in the case where the nitrite is a liquid in which the dialcohol is soluble, such as is the case where the nitrile is acetonitrile. In the case where the nitrite is a solid or a liquid in which the dialcohol fails to dissolve, the reaction can be carried out in a reaction solvent, preferably one in which both the dialcohol and the nitrite are appreciably soluble and with which neither reacts. Suitable solvents include, for example, ketone solvents, such as acetone, and chlorinated hydrocarbon solvents, such as methylene chloride and chloroform. The reaction can be carried out at a temperature from about room temperature to about the reflux temperature of the nitrite or the reaction solvent, preferably, from about 30° C. to about 70° C., and, more preferably, at about 50° C. The duration of the reaction depends, in large measure, on the reactivity of the nitrite, the concentration of the reactants, and other factors. Typically, the reaction is carried out for a period of time from about 5 minutes to about 12 hours, preferably, from about 5 minutes to about 1 hour, and, more preferably, about 20 minutes.

Following the reaction, the diether is isolated. In cases where the diether is insoluble in the reaction medium (i.e., in the nitrile or in the reaction solvent), isolation is best carried out by filtering the precipitated diether, preferably after cooling the reaction mixture. In other cases, the diether can be separated, as an oil or as a precipitate, by addition of a solvent to the reaction mixture of a solvent in which the diether lacks appreciable solubility, typically an alkane, such as petroleum ether, or an ether, such as diethyl ether.

Once the diether is isolated from the reaction mixture, it can be purified, for example, by washing with a solvent, such as acetone, acetonitrile, methanol, and the like. Further purification can be carried out by standard techniques, such as recrystallization or chromatography.

The present invention also relates to a method for preparing betulonic aldehyde. The method starts with betulinol, provided, for example, by the methods described above in connection with preparing the diether of the present invention. Betulinol is then oxidized with chromium anhydride in acetone in the presence of sulfuric acid. In a preferred method, betulinol is first dissolved in acetone, preferably in a weight ratio of from about 1:50 to about 1:200, and more preferably in a weight ratio of from about 1:100 to about 1:110. A mixture of sulfuric acid and chromic anhydride, preferably having a sulfuric acid:chromic anhydride volume ratio of from about 1:2 to about 2:1, more preferably from about 9:10 to about 10:9, and most preferably about 1:1, is then added. The reaction is allowed to proceed at a temperature of from about room temperature to about the reflux temperature of the acetone, preferably at the reflux temperature of the acetone, for from about 15 minutes to about 24 hours, preferably from about 1 hour to about 4 hours, more preferably from about 2.5 to about 3 hours. The reaction can then be worked up by standard procedures to isolate the resulting betulonic aldehyde product. Typically, the reaction mixture is cooled, water is added to it to produce a sediment containing the product, and the sediment is filtered and washed with water to remove residual sulfuric acid. If desired, the filtered betulonic aldehyde can be purified, such as by recrystallization or chromatography, preferably by recrystallization from an alcohol, such as ethanol, isopropanol, or butanol.

The present invention also relates to a compound having the formula:

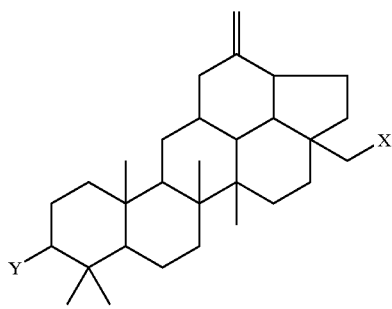

One of X or Y is a -peptide-Q moiety and the other of X and Y is a hydroxy group, an alkoxy group, an alkanoyloxy group, or a -peptide-Q moiety.

Alkoxy groups have the general formula —OR, where R is an alkyl group, defined and illustrated as it was above in connection with the diether of the present invention. For example, suitable alkoxy groups include methoxy, ethoxy, propoxy (including n-propoxy and iso-propoxy), butoxy, pentoxy, and hexoxy (including n-hexoxy and cyclohexoxy). Alkanoyloxy group include those having the general formula —OC(O)R, where R is an alkyl group, defined and illustrated as it was above in connection with the diether of the present invention. For example, suitable alkoxy groups include acetoxy, propionyloxy (including n-propionyloxy and iso-propionyloxy), butanoyloxy, pentanoyloxy, and hexanoyloxy (including n-hexanoyloxy and cyclohexanoyloxy).

As used herein, -peptide-means the diradical of a peptide having the formula H-peptide-OH, where —H denotes the peptide's amino terminus and —OH denotes the peptide's carboxy terminus. The peptide is bonded to the —CH$_2$ group of the betulinol ring structure through its amino terminus. Although the peptide can be made of any amino acid sequence and any number of amino acid residues, it is preferred that the peptide be a tetrapeptide, particularly -Leu-Ala-Leu-Ala-(SEQ ID No: 1), or a pentapeptide, particularly -Gly-Ala-Leu-Gly-Leu-(SEQ ID No: 2).

Q can be a hydroxy group, an —NHNH$_2$ moiety, an —NHNH—C(O)CH$_2$Hal moiety, an -antibody-OH moiety, or an —NHNH—C(O)-antibody-OH moiety.

As used herein, -antibody-OH is a radical form of an antibody having the formula H-antibody-OH, where the H— denotes the amino terminus and the —OH denotes the carboxy terminus of the antibody. Thus, the antibody is bound to the -peptide- moiety or to the -peptide-NHNHC(O)— moiety through its amino terminus.

The preferred type of antibody for use in the invention is an immunoglobulin which is a gammaglobulin. IgG, IgA, IgE, and IgM subclasses are particularly preferred. Some representative immunoglobulins are monoclonal or polyclonal antibodies to human or animal tumor associated antigens; human B- and T-cell antigens; human Ia antigens; viral, fungal and bacterial antigens; and cells involved in human inflammatory or allergic reactions.

Preferred antibodies to human or animal tumor associated antigensinclude: Ig from goats or sheep immunized with carcinoembryonic antigen; Ig from rabbit antiacute lymphoblastic leukemia serum; Ig from various primate antisera raised against acute lymphoblastic leukemia, acute myleoblastic leukemia, chronic lymphoblastic leukemia and chronic granulocytic leukemia; Ig from goats or sheep immunized with lung carcinoma cells, or cellular fractions; monoclonal Ig from mouse hybridomas secreting anti-human colorectal carcinoma antibodies; monoclonal Ig from mouse hybridomas secreting anti-human melanoma antibodies; monoclonal Ig from mouse hybridomas that secrete antibodies reacting with human leukemia cells; monoclonal Ig from mouse hybridomas secreting antibodies reacting with human neuroblastoma cells; monoclonal Ig from mouse hybridomas secreting antibodies reacting with human breast cancer antigens; monoclonal Ig from mouse hybridomas secreting antibodies reacting with human ovarian carcinoma cells; monoclonal Ig from mouse hybridomas secreting antibodies reacting with human osteosarcoma cells, with human pancreatic carcinoma cells, with human prostatic carcinoma cells etc.; monoclonal Ig from mouse hybridomas secreting antibodies to adenocarcinomas including lung, renal, breast and pancreas; monoclonal Ig from mouse hybridomas secreting antibodies reacting with human squamous carcinoma cells; monoclonal Ig from human hybridomas (hybridomas which secrete antibodies to the human tumor associated antigen including, but not limited to, those monoclonals mentioned above; any antibody or fragment thereof that contains carbohydrate in either the light or heavy chain; monoclonal Ig from rat, hamster, or other mammalian species not specifically mentioned above; and Ig from hybridomas which secrete antibodies to human tumor associated antigens including, but not limited to, those mentioned above.

Antibody is also meant to include immunoglobulin fragments Ig', referred to also as Fab, Fab', F(ab')$_2$, and IgM monomer derived from an antibody, for example, by proteolytic enzyme digestion with, for example, pepsin or papain, or by reductive alkylation. Procedures for preparing these antibody fragments are described in Parham, *J. Immunology*, 131:2895 (1983); Lamoyi et al., *J. Immunological Methods*, 56:235 (1983); Parham, *J. Immunological Methods*, 53:133 (1982); and Matthew et al., *J. Immunological Methods*, 50:239 (1982), which are hereby incorporated by reference.

A large number of monoclonal antibodies which are reactive against various tumors or which recognize antigens on the surface of or otherwise associated with tumor cells are known. Illustrative antibodies are provided in Table 1, along with references which further describe the antibody and which are hereby incorporated by reference.

TABLE 1

| Tumor | MoAb | Reference |
|---|---|---|
| Lung | KS1/4 | Varki et al., Cancer Res., 44:681 (1984) |
| | 534,F8;604A9 | Cuttitta et al., in Wright, ed., Monoclonal Antibodies and Cancer, New York:Marcel Dekker, Inc., p. 161 (1984) |
| Squamous Lung Cancer | G1, LuCa2, LuCa3, LuCa4 | Kyoizumi et al., Cancer Res., 45:3274 (1985) |
| Small Cell Lung Cancer | TFS-2 | Okabe et al., Cancer Res., 45:1930 (1985) |
| Colon | 11,285.14 14,95.55 | Rowland et al., Cancer Immunol. Immunother., 19:1 (1985) |
| | NS-31-22, NS-10, NS-19-9,NS-33a, NS-52a, 17-1A | Steplewski et al., Cancer Res., 41:2723 (1981) |
| Melanoma | 9.2.27 | Bumol et al., Proc. Natl. Acad. Sci. (USA), 79:1245 (1982) |
| | p97 | Hellstrom et al., in Wright, ed., Monoclonal Antibodies and Cancer, New York:Marcel Dekker, Inc., p.31 (1984) |
| | R24 | Dippold et al., Proc. Nat'l Acad. Sci. (USA), 77:6114 (1980) |
| Neuroblastoma | P1 153/3 | Kennet et al., 203:1120 (1979) |
| | MIN 1 | Hellstrom et al., in Wright, ed., Monoclonal Antibodies and Cancer, New York:Marcel Dekker, Inc., p.31 (1984) |
| | UJ13A | Goldman et al., Pediatrics, 105:252, 1984. |
| Glioma | BF7, GE2, CG12 | de Tribolet et al., in Wright, ed., Monoclonal Antibodies and Cancer, New York:Marcel Dekker, Inc., p. 81 (1984) |
| Breast | B6.2, B72.3 | Colcher et al., in Wright, ed., Monoclonal Antibodies and Cancer, New York:Marcel Dekker, Inc., p. 121 (1984) |
| Osteogenic Sarcoma | 791T/48, 791T/36 | Embleton, in Wright, ed., Monoclonal Antibodies and Cancer, New York:Marcel Dekker, Inc., p. 181 (1984) and |
| Leukemia | CALL 2 | Teng et al., Lancet, 1:1 (1982). |
| | anti-idiotype | Miller et al., N. Eng. J. Med., 306:517 (1982) |
| Ovary | D83.21, P6.2, Turp-27 | Starling et al., in Wright, ed., Monoclonal Antibodies and Cancer, New York:Marcel Dekker, Inc., p. 253 (1984) |
| Renal | A6H, DSD | Lange et al., Surgery, 98:143 (1985) |

Preferred conjugates are those prepared from monoclonal antibodies, especially those which recognize human cancer cells such as adenocarcinoma, squamous cell carcinoma, transitional cell carcinoma, melanoma, neuroblastoma, small cell carcinoma, leukemia, lymphoma, and sarcoma.

Methods for preparing antibodies and monoclonal antibodies to particular haptenic or antigenic target substrates are described in Goding, *Monoclonal Antibodies: Principles and Practice*, 2nd. ed., New York: Academic Press, (1986); Kennett et al., *Monoclonal Antibodies*, New York: Plenum Press (1980); U.S. Pat. No. 4,423,147 to Secher et al.; U.S. Pat. No. 4,381,292 to Bieber et al.; U.S. Pat. No. 4,363,799 to Kung et al.; U.S. Pat. No. 4,350,683 to Galfre et al.; U.S. Pat. No. 4,127,124 to Clagett et al., which are hereby incorporated by reference.

In particular, the present invention relates to a betulinol-antibody conjugate having the formula:

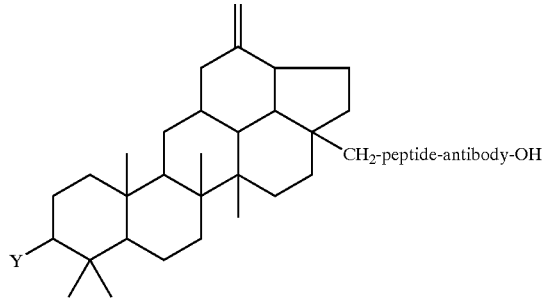

where Y is a hydroxy group, an alkoxy group, or an alkanoyloxy group.

The betulinol-antibody conjugate described in the preceding paragraph is not limited by its method of preparation. One particularly preferred method for preparing the betulinol-antibody conjugate described in the preceding paragraph includes converting a betulinol-peptide derivative having the formula:

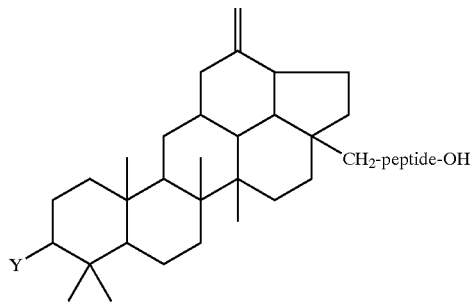

to the betulinol-antibody conjugate with an antibody having the formula H-antibody-OH. The reaction is carried out under conditions effective for formation of a covalent peptide bond between the amino terminus of the antibody and the carboxy terminus of the peptide. Typically, the reaction is carried out using a betulinol-peptide derivative:antibody molar ratio of from about 1:1 to about 100:1; in an inert solvent, such as dimethylformamide; and under mild conditions, such as by gently stirring the reaction mixture at a reduced temperature, preferably from about 0° C. to about 10° C., more preferably about 4° C., for from about 1 hour to about 10 days, preferably for about 3 days. Catalysts typically used in peptide bond formation reactions, such as N,N'-dicyclohexylcarbodiimide ("DCC"), can be used, preferably in a molar amount approximately equal to that of the betulinol-peptide present.

Following the reaction, the crude betulinol-antibody conjugate is isolated, such as by adding water to the reaction mixture to precipitate the product and then filtering the precipitate. Purification of the precipitate can be effected, for example, by chromatography using an appropriate stationary phase, such as silica gel, and a suitable solvent, such as a 4:1 to 1:1 (volume ratio) mixture of chloroform and methanol.

The betulinol-peptide derivative used to produce the betulinol-antibody conjugate can be prepared, for example, from a compound having the formula:

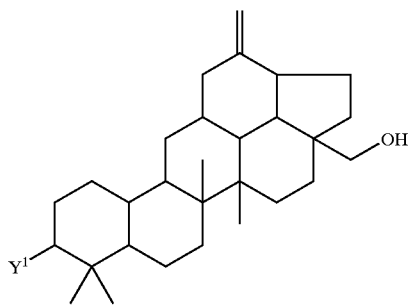

by converting the compound with a peptide having the formula H-peptide-OH.

The reaction is carried out under conditions effective for formation of a covalent bond between the amino terminus of the peptide and the betulinol hydroxy group. Typically, the reaction is carried out using a betulinol compound:antibody molar ratio of about 50:1; in an inert solvent, such as dimethylformamide; and under mild conditions, such as by gently stirring the reaction mixture at a reduced temperature, preferably from about 0° C. to about 10° C., more preferably about 4° C., for from about 1 hour to about 10 days, preferably for about 3 days. Catalysts typically used in peptide bond formation reactions, such as DCC, can be used, preferably in a molar amount approximately equal to the molar amount of betulinol compound present.

Following the reaction, the crude betulinol-peptide can be isolated, for example, by adding water to the reaction mixture to precipitate the product and then filtering the precipitate. Purification of the precipitate can be effected, for example, by chromatography using an appropriate stationary phase, such as silica gel, and a suitable solvent, such as a 4:1 to 1:1 (volume ratio) mixture of chloroform and methanol.

The present invention also relates to a betulinol-antibody conjugate having the formula:

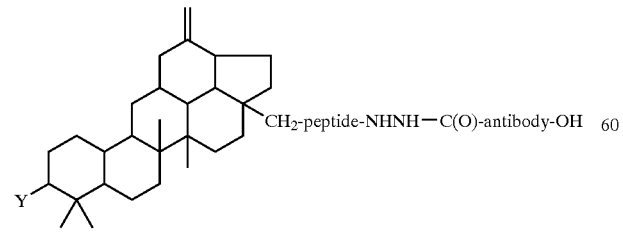

where Y is a hydroxy group, an alkoxy group, or an alkanoyloxy group.

The betulinol-antibody conjugate described in the preceding paragraph is not limited by its method of preparation. However, in one particularly preferred method for preparing the betulinol-antibody conjugate, a haloacetylhydrazide having the formula:

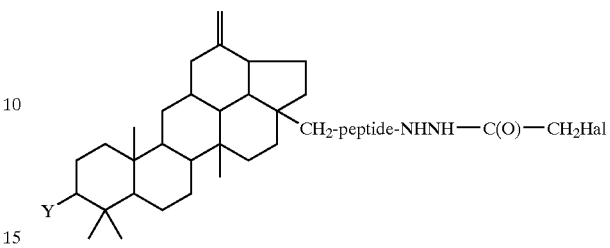

is converted with an antibody having the formula H-antibody-OH under conditions effective to produce the betulinol-antibody conjugate. Hal denotes a halogen atom, such as a chlorine, a bromine, or, preferably, an iodine.

The reaction is carried out under conditions effective for formation of a covalent bond between the amino terminus of the antibody and the NHNHC(O)— moiety. Typically, the reaction is carried out by mixing the haloacetylhydrazide, dissolved in an appropriate solvent, such as DMF, with the antibody, dissolved in an appropriate solvent, such as aqueous buffer. One particularly useful buffer for dissolving the antibody is 0.1 M Tris-HCl buffer, adjusted to a pH of 8 and containing 0.1 M NaCl. The concentrations of the haloacetylhydrazide and antibody in their respective solvents and the amounts of the two solutions employed are selected so that a haloacetylhydrazide:antibody molar ratio of about 1:1 is achieved upon mixing of the two solutions. The conversion can be carried out under mild conditions, such as by gently stirring the reaction mixture at a temperature from about 0° C. to about 70° C., preferably from about 20° C. to about 30° C., more preferably at about 4° C., for from about 1 hour to about 10 days, preferably for about 17 hours.

Following the reaction, the crude betulinol-antibody conjugate is isolated, such as by dialyzing the crude betulinol-antibody conjugate against phosphate buffer, preferably 10 mM, pH 7.2 phosphate buffer containing 0.14 M NaCl. Purification of the isolated betulinol-antibody conjugate can be effected, for example, by chromatography.

The haloacetylhydrazide used to produce the betulinol-antibody conjugate can be prepared by providing a hydrazide having the formula:

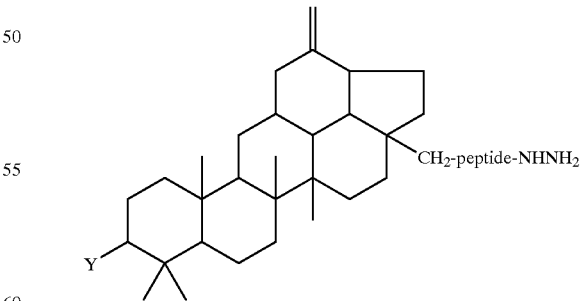

and converting the hydrazide with a p-nitrophenyl haloacetate under conditions effective to produce the haloacetylhydrazide. Nitrophenyl haloacetates suitable for use in this preparative method include p-nitrophenyl chloroacetate, p-nitrophenyl bromoacetate, and, preferably, p-nitrophenyl iodoacetate. The reaction is preferably carried out in a reaction solvent in which both the hydrazide and the p-nitrophenyl haloacetate are soluble, such as DMF or a chlorinated hydrocarbon, such as chloroform. Typically, the hydrazide and the p-nitrophenyl haloacetate are mixed in the reaction solvent, preferably in a hydrazide:p-nitrophenyl haloacetate molar ratio of from about 2:1 to about 1:2, more preferably about 1:1. The reaction mixture is stirred gently, preferably in the dark, at a temperature from about 10° C. to about 100° C., preferably at about room temperature, for a period of time ranging from 1 hour to 3 days, preferably for about 19 hours.

Following the reaction, the crude haloacetylhydrazide is precipitated, preferably after cooling, such as by addition of a solvent, such as ethyl acetate, which reduces the solubility of the haloacetylhydrazide product in the reaction mixture. The precipitate can be collected by any suitable means, such as by filtration or centrifugation. Purification of the precipitate can be effected, for example, by chromatography or recrystallization, but is generally not necessary.

The hydrazide used in the above-described preparation of haloacetylhydrazide can be produced by providing a betulinol-peptide having the formula:

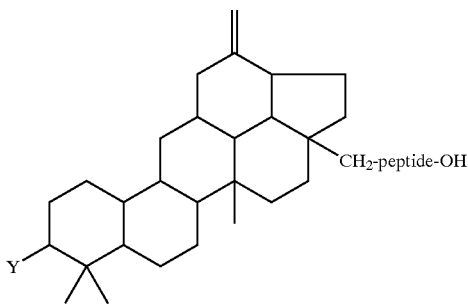

prepared, for example, in accordance with the method described above. The hydrazide preparative method further includes converting the betulinol-peptide with hydrazine hydrate under conditions effective to produce the hydrazide. The reaction is preferably carried out in a reaction solvent in which both hydrazine hydrate and the betulinol-peptide are soluble, such as DMF or a chlorinated hydrocarbon, such as chloroform. Typically, the hydrazine hydrate and the betulinol-peptide are mixed in the reaction solvent, preferably in a hydrazine hydrate:betulinol-peptide molar ratio of from about 2:1 to about 1:2, more preferably about 1:1. The reaction mixture is stirred, preferably at a temperature from about 10° C. to about 100° C., more preferably at about room temperature, for a period of time ranging from 12 hours to about 10 days, preferably for about 5 days.

Following the reaction, the crude hydrazide is precipitated, preferably after cooling, such as by addition of a solvent, such as ethyl alcohol, which reduces the solubility of the hydrazide product in the reaction mixture. The precipitate can be collected by any suitable means, such as by filtration or centrifugation. Purification of the precipitate can be effected, for example, by chromatography or recrystallization, but is generally not necessary.

The present invention also provides a betulinol-antibody conjugate having the formula:

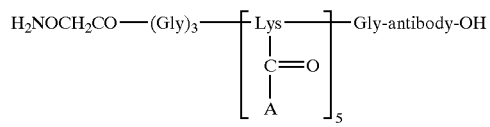

A are independently selected from an aldehyde group or a moiety having the formula:

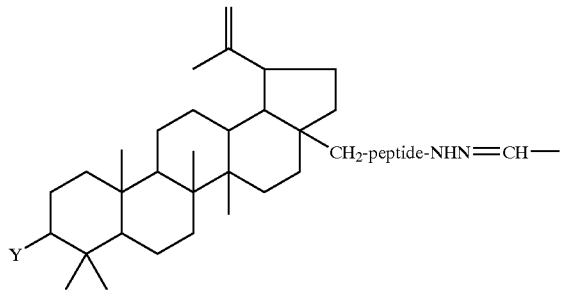

provided that at least one of A is not an aldehyde group. Y can be a hydroxy group, an alkoxy group, or an alkanoyloxy group.

The betulinol-antibody conjugate described in the preceding paragraph can be made by providing a carrier molecule having the formula:

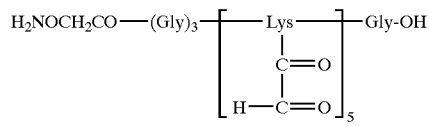

The carrier molecule is then converted with a hydrazide having the formula:

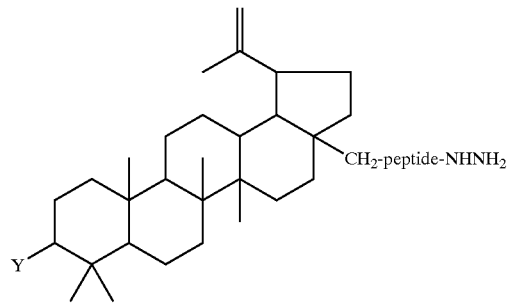

and with an antibody having the formula H-antibody-OH under conditions effective to produce the betulinol-antibody conjugate.

The order of reaction is not critical to the practice of the present invention. For example, the carrier molecule can be reacted with the antibody under conditions effective to produce an antibody-bound carrier molecule having the formula:

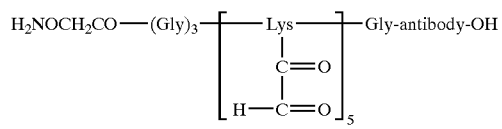

The antibody-bound carrier molecule is then reacted with the hydrazide under conditions effective to produce the betulinol-antibody conjugate.

Alternatively, the carrier molecule can be reacted with the hydrazide under conditions effective to produce a betulinol-bound carrier molecule having the formula:

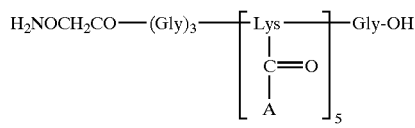

where at least one A is a moiety having the formula:

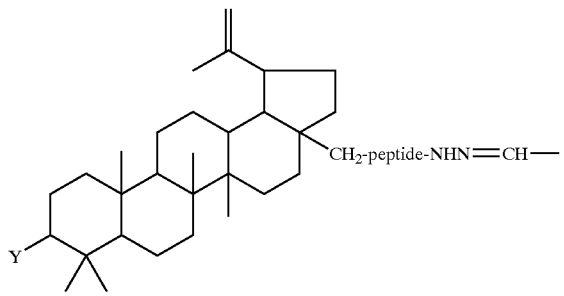

The betulinol-bound carrier molecule is then reacted with the antibody under conditions effective to produce the betulinol-antibody conjugate.

In either case, reaction of the antibody with the Gly residue of the carrier molecule or betulinol-bound carrier molecule can be carried out under conditions effective for formation of a covalent peptide bond between the amino terminus of the antibody and the carboxy group of the Gly residue. Typically, the reaction is carried out using a carrier molecule:antibody molar ratio of from about 1:1 to about 10:1; in an inert solvent, such as dimethylformamide; and under mild conditions, such as by gently stirring the reaction mixture at a reduced temperature, preferably from about 0° C. to about 10° C., more preferably about 4° C., for from about 1 hour to about 10 days, preferably for about 3 days. Catalysts typically used in peptide bond formation reactions, such as DCC, can be used, preferably in a molar amount approximately equal to that of the antibody present.

Following the reaction, the crude antibody-bound carrier molecule product or the crude betulinol-antibody conjugate product is isolated, such as by adding water to the reaction mixture to precipitate the product and then filtering the precipitate. Purification of the precipitate can be effected, for example, chromatographically using an appropriate stationary phase, such as silica gel, and solvent such as a 4:1 to 1:1 (volume ratio) mixture of chloroform and methanol.

Reaction of the aldehyde group on the carrier molecule or on the antibody-bound carrier molecule with the hydrazide is best carried out under conditions which are conducive for the formation of hydrazone bonds. The number of aldehyde residues which react with hydrazide (and, thus, the number of A moieties attached to the carrier molecule) depends primarily on the molar ratio of hydrazide to carrier molecule. Suitable hydrazide:carrier molecule molar ratios range from about 1:1 to about 20:1. The reaction is carried out in an inert solvent, such as DMF by stirring the reaction mixture at a temperature from about 15° C. to about 35° C., preferably about 25° C., for from about 10 hours to about 6 days, preferably for about 5 days. Further details regarding this reaction are described, for example, in Vilaseca et al., *Bioconjugate Chem.*, 4:515–520 (1993) ("Vilaseca"), which is hereby incorporated by reference.

Following the reaction, the crude betulinol-bound carrier molecule product or the crude betulinol-antibody conjugate product is isolated, such as by precipitation with butanol followed by centrifugation or filtration. Purification of the precipitate can be effected, for example, by chromatography.

The carrier molecule can be prepared by the method described in Vilaseca, which is hereby incorporated by reference. Briefly, the resin-bound protected nonapeptide Fmoc-Gly$_3$-[Lys(t-Boc)]$_5$-Gly-OCH$_2$-PAM (SEQ ID No: 3), resin is synthesized by standard fluorenylmethyloxycarbonyl ("Fmoc") techniques from a t-Boc-Gly-OCH$_2$-PAM ((phenylacetaimido)methyl resin) on an automated peptide synthesizer. The protected nonapeptide is then deprotected with trifluoroacetic acid ("TFA") and reacted with t-Boc-Ser(Bzl)-OSu to produce Fmoc-Gly$_3$-[Lys(t-Boc-Ser(Bzl))]$_5$-Gly-OCH$_2$-PAM (SEQ ID No: 4). Deprotection with piperidine in DMF followed by deprotection with TFA and reaction with t-Boc-NHOCH$_2$COOSu yields t-Boc-NHOCH$_2$CO-Gly$_3$-[Lys(t-Boc-Ser(Bzl))]5-Gly-OCH$_2$-PAM (SEQ ID No: 5). Treatment of this material with TFA and then with a mixture of TFA and trifluoromethanesulfonic acid produces the carrier molecule.

The present invention also relates to a betulinol-antibody conjugate having the formula:

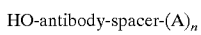

A is a moiety having the formula:

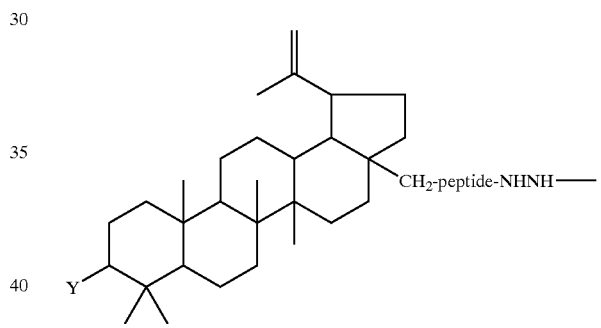

Y is a hydroxy group, an alkoxy group, or an alkanoyloxy group, suitable examples of which include those described above, and n is an integer from 1 to 100, preferably from 30 to 50.

The spacer moiety is functionalized with groups capable of bonding with the —NHNH— group of the A moiety. Each of the moieties A are attached to the spacer. Each A can be incorporated into the backbone of the spacer, or, alternatively, each A can be attached to the spacer backbone as a pendant group.

For example, the -spacer-(A)$_n$ moiety can have the formula:

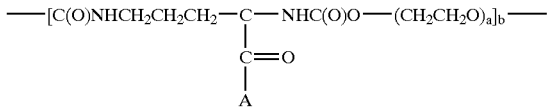

where a is an integer from 1 to 100, and b is an integer equal to n. Alternatively, the spacer can be a diamine derivative of polyethylene glycol having 2-(pyridyldithio)-propionyl and N-hydroxysuccinimide ester groups bonded thereto, such as those described in Haselgrubler et al., *Bioconjugate Chem.*, 6:242–248 (1995) ("Haselgrubler"), which is hereby incorporated by reference. Another spacer suitable for use in practicing the present invention is a branched form of polyethylene glycol propionic acid N-hydroxysuccinimide ester, such as a monomethoxypoly(ethylene glycol)-propionic acid N-hydroxysuccinimide ester. This and other branched forms of polyethylene glycol propionic acid N-hydroxysuccinimide ester are described in Senter et al., *Bioconjugate Chem.*, 6:389–394 (1995) ("Senter"), which is hereby incorporated by reference.

The betulinol-antibody conjugates described in the preceding paragraphs can be prepared by providing a crosslinker having a first reactive terminus and one or more second reactive termini. The first reactive terminus is reacted with an antibody, and one or more of the one or more second reactive termini is reacted with a hydrazide having the formula:

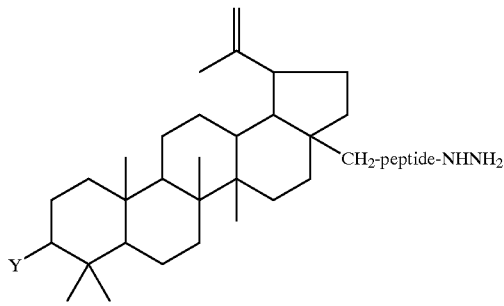

The hydrazide can be prepared by the methods described above.

Suitable crosslinkers for the practice of the present invention include molecules which contain functional groups capable of forming covalent bonds with an antibody and with the hydrazide. The first terminus is typically an amino group (capable of reacting with the antibody's carboxy terminus) or a hydroxyl, an aldehyde, or a carboxylic acid group (capable of reacting with the antibody's amino terminus). The crosslinker can be a polymer containing pendant groups having the required reactivity.

One suitable crosslinker is poly(polyethylene glycol-lysine), which has the formula:

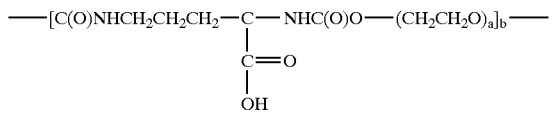

The poly(polyethylene glycol-lysine) can be prepared from lysine and polyethylene glycol by the methods described in Vilaseca; Poiani et al., *Biocongugate Chem.*, 5:621–630 (1994); Nathan et al., *Bioconjugate Chem.*, 4:54–62 (1993); Nathan et al., *Macromolecules*, 25:4476–4484 (1992); and Nathan et al., *Am. Chem. Soc. Polym. Preprints*, 31:213–214 (1990), which are hereby incorporated by reference.

Other suitable crosslinkers are diamine derivatives of polyethylene glycol having 2-(pyridyldithio)-propionyl and N-hydroxysuccinimide ester groups bonded thereto, such as those described in Haselgrubler, which is hereby incorporated by reference. Another crosslinker suitable for use in practicing the present invention is a branched form of polyethylene glycol propionic acid N-hydroxysuccinimide ester, such as a monomethoxypoly(ethylene glycol)-propionic acid N-hydroxysuccinimide ester. Further description of and methods for preparing these polyethylene glycol propionic acid N-hydroxysuccinimide esters is provided in Senter, which is hereby incorporated by reference.

The hydrazide can be prepared by the methods described above.

Reaction of the first reactive terminus of the crosslinker with the antibody is typically carried out in an inert solvent, such as dimethyl sulfoxide ("DMSO"), by stirring the reaction mixture at a temperature from about 19° C. to about 25° C., preferably about 19° C., for from about 60 minutes to about 120 minutes, preferably for about 70 minutes. Suitable antibody:crosslinker molecule molar ratios range from about 1:1.5 to about 1:12. Further details regarding this reaction are described, for example, in Haselgrubler, which is hereby incorporated by reference.

Reaction of the second reactive terminus of the crosslinker with the hydrazide is typically carried out in an inert solvent, such as DMSO, by stirring the reaction mixture at a temperature from about 19° C. to about 25° C., preferably about 19° C. for from about 60 minutes to about 120 minutes, preferably for about 70 minutes. The number of hydrazide moieties which react with each crosslinker molecule (and, thus, the number of A moieties attached to the spacer) depends primarily on the molar ratio of hydrazide to crosslinker. Suitable hydrazide:crosslinker molecule molar ratios range from about 1:1.5 to about 1:12. Further details regarding this reaction are described, for example, in Haselgrubler, which is hereby incorporated by reference.

The reaction can be carried out in any order. Thus, the first reactive terminus can be coupled to the antibody, and the second reactive termini of the resulting antibody-crosslinker product can then be reacted with the hydrazide. Alternatively, the hydrazide can be reacted with the second reactive termini of the crosslinker, and the first reactive terminus of the resulting hydrazide-crosslinker complex can then be reacted with the antibody. A simultaneous, one pot reaction of the crosslinker, antibody, and hydrazide is also contemplated, although purification of the betulinol-antibody conjugate may be more difficult.

Following each reaction, the crude hydrazide-crosslinker intermediate or the crude antibody-crosslinker intermediate can be isolated, such as by precipitation with butanol. In addition, the intermediate hydrazide-crosslinker or antibody-crosslinker can also be purified, for example, by chromatography. Alternatively the crude hydrazide-crosslinker intermediate or the crude antibody-crosslinker intermediate can be reacted with the antibody or hydrazide, respectively, without purification.

The crude betulinol-antibody conjugate produced by the above-described process can be isolated such as by precipitation with butanol. In addition, the isolated betulinol-antibody conjugate can also be purified, for example, by chromatography.

The present invention also relates to a method of treating cancer by administering to a cancer patient an effective amount of a betulinol derivative.

Suitable betulinol derivatives include betulonic aldehyde. They also include compounds having the formulae:

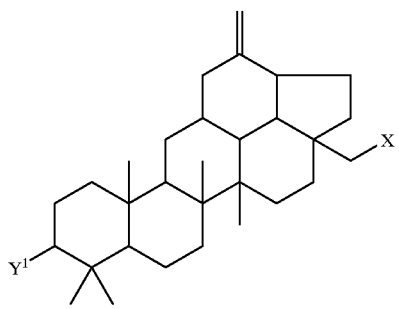

where X and $Y^1$ are each independently selected from the group consisting of a hydroxy group, an alkoxy group, an alkanoyloxy group, a -peptide-antibody-OH moiety, and -peptide-NHNH—C(O)-antibody-OH moiety, such as betulinol dimethyl ether and betulinic acid diacetate. Other suitable betulinol derivatives include the betulinol-antibody conjugates of the present invention. In each of these betulinol derivatives, HO-antibody-H is an antibody targeted to a site to be treated in the patient. Suitable antibodies include those cited above.

The betulinol derivatives can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form, such as tablets, capsules, powders, solutions, suspensions, or emulsions.

The solid unit dosage forms can be of the conventional type. The solid form can be a capsule, such as an ordinary gelatin type containing the betulinol derivative and a carrier, for example, lubricants and inert fillers, such as lactose, sucrose, or cornstarch. In another embodiment, these betulinol derivatives can be tableted with conventional tablet bases, such as lactose, sucrose, or cornstarch, in combination with binders, like acacia, cornstarch, or gelatin, disintegrating agents, such as cornstarch, potato starch, or alginic acid, and lubricants, like stearic acid or magnesium stearate.

The betulinol derivatives may also be administered in injectable dosages by solution or suspension of these materials in a physiologically acceptable diluent with a pharmaceutical carrier. Such carriers include sterile liquids, such as water and oils, with or without the addition of a surfactants, adjuvants, excipients, or stabilizers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

For use as aerosols, the betulinol derivative in solution or suspension may be packaged in a pressurized aerosol container together with suitable propellants, for example, hydrocarbon propellants like propane, butane, or isobutane, and with conventional adjuvants. The betulinol derivatives can also be administered in a non-pressurized form, such as in a nebulizer or atomizer.

The present invention is further illustrated by the following examples.

EXAMPLES

Example 1

Preparation of Betulinol Biacetate

Betulinol was placed in a reactor, and acetic anhydride was then added with stirring. After the addition, the molar ratio of betulinol to acetic anhydride was between 1:20 and 1:50. The reaction mixture was then heated with stirring to 139–141° C., maintained at this temperature for between 60 and 90 min, and then cooled to 110–120° C. Hot water, in an amount equal to 6–10 times the initial mass of betulinol, was then added with stirring. A crystalline sediment formed, and the sediment was removed by filtration and flushed repeatedly with hot water until the pH of the filtrate reached 6.8–7.0. The sediment of betulinol biacetate was then dried at 60–70° C. and purified by recrystallization in an organic solvent (acetone, ethyl acetate, isopropyl alcohol, or butyl alcohol). Briefly, recrystallization was carried out by diluting the betulinol biacetate in the solvent with heating, boiling the betulinol acetate solution for from 0.5 to I hour, and cooling the betulinol biacetate solution to 10–15° C. A sediment formed, was filtered, and, was dried. The resulting product was 97–98% betulinol biacetate and had a melting temperature of 215° C. The yield of purified betulinol biacetate was 90%.

Alterations of the betulinol-acetic anhydride mole ratios from 1:20 to 1:50 showed that substantial acetic anhydride surplus had no considerable effect on the betulinol biacetate ("BBA") yield and purity. The results obtained in the above experiment are illustrated in Table 2.

TABLE 2

Effect of Betulinol-Acetic Anhydride Mole Ratio on Product Outcome and Purity

| Parameter | 1:20 | 1:30 | 1:40 | 1:50 |
|---|---|---|---|---|
| Main Substance Purity, % | 94.6 | 93.2 | 95.3 | 96.0 |
| Mass Contents of Hydroxyl Groups, % | 6.9 | 6.8 | 7.1 | 7.1 |
| Melting Temperature (° C.) | 208–210 | 207–209 | 208–210 | 207–209 |
| Actual Outcome, % | 95.0 | 95.2 | 95.1 | 96.0 |

Since increasing betulinol-acetic anhydride mole ratio was proven to noticeably affect neither the yield nor the purity of the final product, all subsequent experiments were conducted at the fixed mole ratio of 1:20. Increasing the etherification time did not produce any considerable effect on the outcome and purity of the biacetate ether (See Table 3).

TABLE 3

Effects of Altering the Etherification Time and Effect on the Yield abd Purity of BBA

| Time Etherification (min) | Ether Number (mg KOH/g) | Mass Contents of Hydroxyl Groups (%) | Main Substance Purity (%) | Actual Yield (%) |
|---|---|---|---|---|
| 5 | 193 | 6.7 | 90.6 | 92.5 |
| 10 | 198 | 6.8 | 90.8 | 94.0 |
| 20 | 201 | 7.1 | 93.8 | 94.1 |
| 30 | 198 | 6.9 | 92.8 | 94.8 |
| 40 | 200 | 7.1 | 93.7 | 92.5 |
| 50 | 198 | 6.9 | 93.0 | 95.4 |
| 60 | 203 | 7.2 | 94.0 | 96.1 |

It was noticed that the quality of the "commercial" biacetate depended on the way it was extracted from the reaction mixture (See Table 4). The best results were obtained during Experiment 1 when hot water was stirred into the reaction mixture so that the BBA-water mass ratio was 1:6. The reaction mixture was then cooled to 110–120° C., and the resulting residue was then filtered and washed with hot water. In Sample 3, addition of water to the reaction mixture after it had completely cooled off and crystalline residue had formed proved to slightly decrease the mass contents of the main substance and cause deterioration of its visual appearance.

TABLE 4

BBA Extraction Results

| BBA Parameters[a] | | | | Mass BBA | |
|---|---|---|---|---|---|
| AN | SN | EN | —OH | Contents | Method of Extraction |
| Experiment 1 | | | | | |
| 7.2 | 205.6 | 198.4 | 7.0 | 93.9 | poured reaction mixture into hot water (110–120° C.) |
| Experiment 2 | | | | | |
| 11.2 | 200.5 | 188.5 | 6.9 | 93.8 | poured reaction mixture onto cold water (110–120° C.) |
| Experiment 3 | | | | | |
| 4.0 | 197.4 | 193.4 | 6.7 | 90.8 | poured reaction mixture into cold water after the residue had formed (20–30° C.) |

[a]AN is Acid Number (mg KOH/g);
SN is Saponification Number (mg KOH/g);
EN is Ether Number (mg KOH/g);
—OH, % is mass contents of hydroxyl groups.

Studies of betulinol biacetate solubility were conducted in order to determine the appropriate solvent for product crystallization and purification. The results of these studies are shown in Table 5.

TABLE 5

BBA Solubility at 20° C. and Other Selected Temperatures (mass % in organic solvents)

| Solvent | BBA Mass Content, %, at 20° C. | T (° C.) | BBA Mass Content, %, at T (° C.) |
|---|---|---|---|
| Acetone | 32 | 56 | 68 |
| Hexane | 15 | 69 | 52 |
| Ethylacetate | 53 | 77 | 100 |
| Ethanol | 2.8 | 78 | 18 |
| Butanol | 15 | 95 | 100 |
| Isopropanol | 6.5 | 82 | 72 |
| Benzene | 100 | | |
| Chloroform | 100 | | |
| Dioxane | 30 | 101 | 100 |
| Dimethylsulfoxide | 30 | 189 | 100 |
| Toluene | 100 | | |

Of the solvents listed in Table 5, only acetone, ethylacetate, isopropanol and butanol were selected for crystallization experiments. Additional BBA crystallization and purification was observed to increase the biological activity of the product. For re-crystallization experiments, BBA with the acid number of 10–12 and purity of 90–93% was used. The results of such experiments are shown in Table 6.

TABLE 6

BBA Re-Crystallization

| | Main Fraction | | Remainder after Crystallization | | |
|---|---|---|---|---|---|
| Solvent | Outcome % | BBA Mass Contents, % | Color | Yield % | BBA Mass Content, % |
| Acetone | 52 | 92 | yellowish | 27.6 | 83 |
| Ethylacetate | 40 | 91 | Yellowish | 47.3 | 85.9 |
| Isopropanol | | | | | |
| 1st Crystallization | 76 | 93.4 | yellowish | 11.4 | 86 |
| 2nd Crystallization | 91.8 | 95.8 | yellowish | 7.5 | 89 |
| Butanol | | | | | |
| 1st Crystallization | 83.9 | 95.8 | white | 9.3 | 88.3 |
| 2nd Crystallization | 87.0 | 97.2 | white | 5.9 | 89 |

To obtain a representative sample for further medical testing, butanol was selected as a solvent. The BBA sample had a melting temperature of 217° C. and BBA mass content of 97.0%.

Example 2

Preparation of Betulonic Aldehyde

Betulinol was placed in a thermostated reactor, and acetone, in an amount of 100–110 ml per gram of betulinol, was added with stirring. An oxidizing mixture of $CrO_3/H_2SO_4$ (molar ratio of 2:3, respectively) was then slowly poured into the reactor 20 with stirring. The reaction mixture was brought to reflux and maintained at reflux for 2.5–3 hrs. The reaction mixture was then cooled and water was added, resulting in the formation of a sediment. The sediment was filtered and recrystallized from ethanol. The resulting solid contained 93–95% of betulonic aldehyde and melted at a temperature from 154–156° C. The yield of purified betulonic aldehyde was 65%.

Example 3

Preparation of Cornelon

Betulinol was dissolved in acetonitrile in a betulinol-to-acetonitrile mole ratio of 1:40. The solution was heated to 50° C. and stirred for 20 minutes. The crystalline residue, designated as "Cornelon", was washed with acetonitrile, filtered, and dried at 60° C. Cornelon was obtained in a 80–95% yield and was analyzed by HPLC.

Example 4

Anti-Carcinogenic Activity of Betulinol Biacetate and Betulonic Aldehyde

The anti-carcinogenic activity of betulinol biacetate and betulonic aldehyde was assessed using 117–120 gram white rats implanted with worker's carcinoma and 21–23 gram white mice with artificially transplanted Ehrlich's tumor.

Solutions of 2.5% betulonic aldehyde and 0.05% betulinol biacetate were prepared in 10% polyvinylpyrrolidone containing Tween-80 (a sorbitan mono-9-octadecenate poly (oxy-1,2-ethanediyl)) stabilizer.

Mice were injected with 0.1–0.2 ml of either betulinol biacetate or betulonic aldehyde solution daily, starting 24 hours after transplantation, for the following 5 days. Rats were injected with 1.2 ml of either betulinol biacetate or betulonic aldehyde solution daily, starting 24 hours after implantation, for the following 5 days. Animals in control groups received the same amount of a 10% solution of polyvinylpyrrolidone.

The anti-tumor effect of betulinol acetate or betulonic aldehyde was determined by measuring the volume of the tumor on the 10th day after implantation. An average length of life ("ALL") was calculated for each of the deceased animals. In addition, the percentage of cured rats was also determined.

The volume of the tumor was measured and calculated as a multiple of the quadrate of its similar diameter by the greater diameter. Thus, the effect was expressed as a ratio ("E/C"), in percent, of the tumor volume in rats treated with betulinol acetate or betulonic aldehyde ("E") and the tumor volume in control rats ("C"). The effect of betulinol acetate or betulonic aldehyde on ALL was evaluated the same way.

A total of 155 mice and 142 rats were used for these experiments. The experimental results are shown in Table 7.

TABLE 7

Anticarcinogenic Effect of Betulinol Diacetate and Betulon Aldehyde

WALKER-CARCINOMA (carcinosarcoma) (28 Rats/Group)

| Fraction Injected (mg/kg body weight) | Dose/day | ALL[1] (days) | % cured | % of control[2] |
|---|---|---|---|---|
| Betulinol diacetate | | | | |
| Group 1 | 204.6 | 28.5 | 50.0 | 131.3 |
| Group 2 | 106.9 | 43.5 | 67.0 | 200.5 |
| Control Group | 0.0 | 21.7 | 0.0 | 100% |
| Betulon aldehyde | | | | |
| Group 1 | 102.6 | 26.5 | 33.0 | 122.1 |
| Control Group | 0.0 | 21.7 | 0.0 | 100.0 |

EHRLICH-LETTRE CARCINOMA (17 Mice/Group)

| Fraction Injected (mg/kg body weight) | Dose/day | ALL[1] (days) | % of control |
|---|---|---|---|
| Betulon aldehyde | | | |
| Group 1 | 206.7 | 12.5 | 118.0 |
| Group 2 | 197.0 | 10.5 | 99.1 |
| Group 3 | 98.0 | 11.0 | 103.7 |
| Control Group | 0.0 | 10.6 | 100.0 |

[1] ALL-Average length of life
[2] Cured rats lived over two months after implantation of sarcoma.

It was found that the tested substances showed high anti-carcinogenic activity. On the 10th day after the injection, the rate of the tumor growth was inhibited as much as 55.2% of the control group, by betulinol biacetate and 31.2% by Betulon aldehyde. Further, many animals showed complete disappearance of the tumor and total recovery.

Example 5

Hypothetical Conjugation of the Betulinol with Pentapeptide

N,N'-dicyclohexylcarbodiimide ("DCC") (206 mg) and a pentapeptide, gly-ala-leu-gly-leu, (360 mg) will be dissolved in 30 ml of DMF. The DMF solution will then be added to betulinol (499 mg). The mixture will be stirred for 3 days at 4° C. Two ml of ice water will be added, and the precipitate which forms will be removed by filtration. The filtrate will be evaporated and subjected to chromatography on a silica gel column (3×30 cm, YMC-Gel, SIL60, 350/250 mesh) with chloroform:methanol (4:1), to isolate the pentapeptide ester derivative of betulinol (expected yield: 500 mg). The product will be analyzed by preparative think layer chromatography on silica gel-coated glass plates eluted with a mixture of chloroform-methanol-water (120:20:1, v/v/v), and by amino acid analysis. The major fraction containing the betulinol-peptide conjugate will be utilized for further linking with an antibody.

Example 6

Hypothetical Preparation of Betulinol-Antibody Conjugate

The monoclonal antibody will be succinylated as follows. 10 mg of the antibody will be dissolved in 0.1 ml of water, and the pH will be adjusted to 7.5. Succinic anhydride (0.068 mmole) will be added while maintaining the pH at 7.5. Another aliquot of 0.068 mmole of succinic anhydride will be added, and the solution will be extensively dialyzed against phosphate buffered saline ("PBS") buffer.

The betulinol-pentapeptide (20 μmole, in DMF) will be mixed with 50 mg of the succinylated antibody and 7.5 mg of 1-ethyl-3-(3-dimethylaminopropyl) carbodiimide hydrochloride. The mixture will be incubated overnight at 25° C. Any unconjugated drug present will be removed by treating the reaction mixture with activated charcoal (0.3 mg/mg protein) for 1 hr at 4° C. The mixture will be extensively dialyzed against 10 mM phosphate buffer, pH 7.2, containing 0.15 M NaCl, to give a betulinol-pentapeptide-antibody conjugate. The conjugate will be purified by HPLC and characterized for its homogeneity and properties. The conjugates will be further characterized by nuclear magnetic resonance and by sodium dodecyl sulfate polyacrylamide gel electrophoresis ("SDS-PAGE").

Example 7

Hypothetical Preparation of Betulinol-Antibody Conjugate

DCC (206 mg) will be added to a solution of betulinol (499 mg) and tetrapeptide (360 mg) in 30 mg of DMF. The mixture will be stirred at 4° C. for 3 days. Ice-water (2 ml) will then be added to generate a precipitate, which is then removed by filtration. The filtrate will then be evaporated, and the residue will be subjected to medium pressure chromatography on a silica gel column (3×30 cm, YME-GEL, SIL60, 350/250 mesh) with chloroform-methanol (4:1 to 1:1). The tetrapeptide ester derivative of betulinol is isolated as a powder (500 mg) by evaporation of the solvent, treatment with ethyl acetate and filtration.

Hydrazine hydrate (500 mg) will be mixed with a solution of the tetrapeptide ester derivative of betulinol (418 mg) in 20 ml of DMF, and the mixture will be stirred at room temperature for 5 days. A small amount of precipitate which forms will be removed by centrifugation, and the mixture will be treated with 50 ml of ethanol. The resulting precipitate (a belulinol tetrapeptide hydrazide derivative will be collected by filtration and dried under reduced pressure.

p-Nitrophenyl iodoacetate (61 mg) will be added to a solution of the belulinol tetrapeptide hydrazide derivative (100 mg) in DMF (2 ml), and the mixture will be stirred at room temperature for 19 hr. in the dark. The mixture is then treated with ethyl acetate (30 ml), which causes a precipitate to form. The precipitate will be collected by centrifugation and dried under reduced pressure to give the iodoacetylhydrazide derivative of the betulinol tetrapeptide (105 mg).

A solution of the iodoacetylhydrazide derivative of the betulinol tetrapeptide in DMF (48.8 mg/ml) will be added to a solution of antibody in 0.1 M Tris-HCl buffer (pH 8.0, containing 0.1 M NaCl) (8.27 mg/ml), and the mixture will be allowed stand at 25° C. for 17 hr. The mixture will then extensively dialyzed against 10 mM PBS to give the betulinol-antibody conjugate.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A diether having the formula:

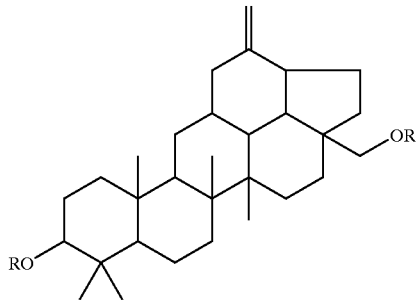

wherein R is an alkyl group other than methyl.

2. A method of synthesizing a diether having the formula:

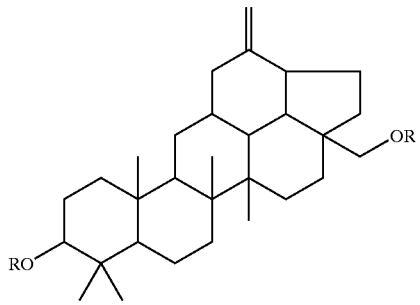

wherein R is alkyl, said method comprising:

alkylating a dialcohol having the formula:

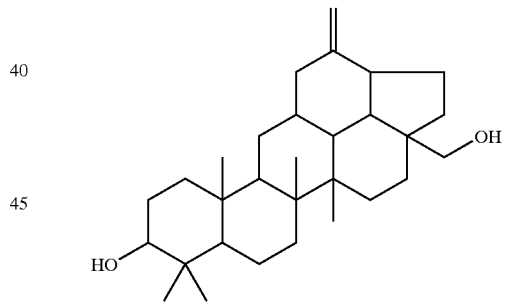

with a nitrile having the formula:

R—C≡N for a time and under conditions effective to form the diether, and isolating the diether.

3. A method according to claim 2, wherein R is methyl.

4. A method according to claim 2, wherein the dialcohol and the nitrile, respectively, are present in a mole ratio of from about 1:20 to about 1:60.

5. A method according to claim 2, wherein said alkylating is carried out at a temperature of from about 30° C. to about 70° C.

6. A method of preparing betulonic aldehyde comprising:
oxidizing betulinol with chromium anhydride in acetone in the presence of sulfuric acid for a time and under conditions effective to produce betulonic aldehyde, and isolating the betulonic aldehyde.

7. A method according to claim 6, wherein the betulinol and acetone, respectively, are present in a weight ratio of from about 1:100 to about 1:110.

8. A method according to claim 6, wherein the chromium anhydride and sulfuric acid, respectively, are present in a molar ratio of from 9:10 to about 10:9.

9. A method of preparing betulonic aldehyde comprising:

reacting betulinol with chromium anhydride in acetone in the presence of sulfuric acid for a time and under conditions effective to produce a reaction mixture that includes betulonic aldehyde;

cooling the reaction mixture;

adding water to the reaction mixture, whereby a sediment containing betulonic aldehyde forms; and isolating the betulonic aldehyde.

10. A method of preparing betulonic aldehyde comprising:

reacting betulinol with chromium anhydride in acetone in the presence of sulfuric acid for a time and under conditions effective to produce a reaction mixture that includes betulonic aldehyde;

cooling the reaction mixture;

adding water to the reaction mixture, whereby a sediment containing betulonic aldehyde forms;

crystallizing the sediment; and isolating the betulonic aldehyde.

11. A compound having the formula:

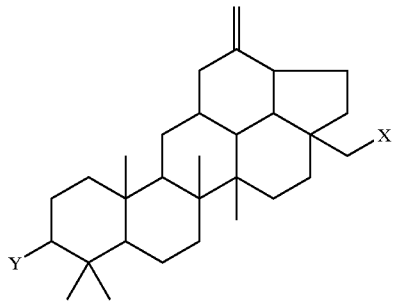

wherein

X or Y is a -peptide-Q moiety and the other of X and Y is a hydroxy group, an alkoxy group, an alkanoyloxy group, or a -peptide-Q moiety;

Q is a hydroxy group, a —$NHNH_2$ moiety, an —$NHNH-C(O)CH_2Hal$ moiety, an -antibody-OH moiety, or an —NHNH-C(O)-antibody-OH moiety; and Hal is a halogen.

12. A compound according to claim 11, wherein "-peptide-" is a pentapeptide.

13. A compound according to claim 12, wherein the pentapeptide is -Gly-Ala-Leu-Gly-Leu-(SEQ ID NO: 2).

14. A compound according to claim 11, wherein "-peptide-" is a tetrapeptide.

15. A compound according to claim 14, wherein the tetrapeptide is -Leu-Ala-Leu-Ala-(SEQ ID NO: 1).

16. A method of producing a betulinol-antibody conjugate having the formula:

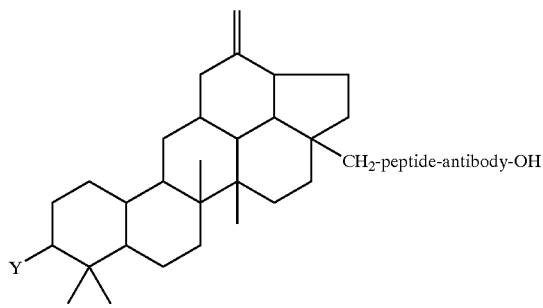

wherein

Y is a hydroxy group, an alkoxy group, or an alkanoyloxy group, said method comprising:

reacting a betulinol peptide having the formula:

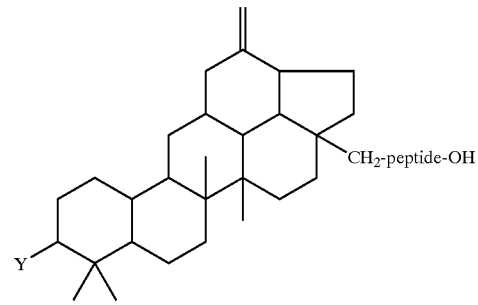

with an antibody having the formula H-antibody-OH for a time and under conditions effective to produce the betulinol-antibody conjugate, and isolating the betulinol-antibody conjugate.

17. A method according to claim 16, wherein -peptide- is a pentapeptide.

18. A method according to claim 17, wherein the pentapeptide is -Gly-Ala-Leu-Gly-Leu-(SEQ ID NO: 2).

19. A method according to claim 16, wherein -peptide- is a tetrapeptide.

20. A method according to claim 19, wherein the tetrapeptide is -Leu-Ala-Leu-Ala-(SEQ ID NO: 1).

21. A method according to claim 16, wherein said betulinol peptide is obtained by a process comprising:

reacting a compound having the formula:

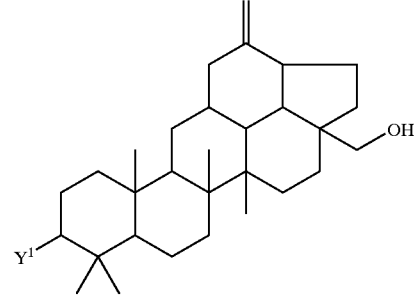

with a peptide having the formula H-peptide-OH for a time and under conditions effective to produce the betulinol peptide, and isolating the betulinol peptide.

22. A method of producing a betulinol-antibody conjugate having the formula:

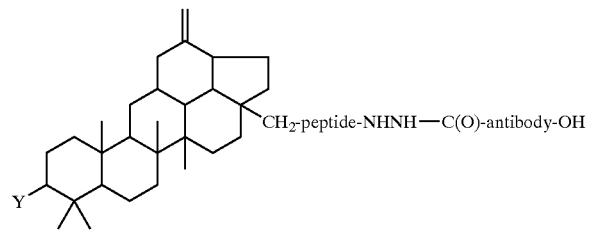

wherein
  Y is a hydroxy group, an alkoxy group, or an alkanoyloxy group,
said method comprising:
  reacting a haloacetyihydrazide having the formula:

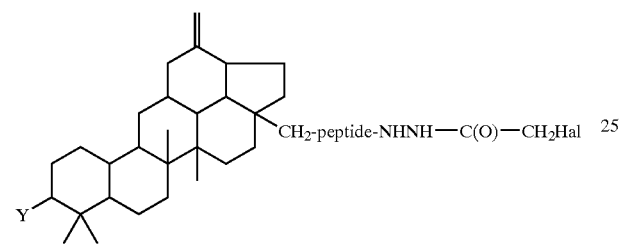

wherein
  Hal is a halogen
with an antibody having the formula H-antibody-OH for a time and under conditions effective to produce the betulinol-antibody conjugate, and
  isolating the betulinol-antibody conjugate.

23. A method according to claim 22, wherein Hal is I.

24. A method according to claim 22, wherein "-peptide-" is a pentapeptide.

25. A method according to claim 24, wherein the pentapeptide is -Gly-Ala-Leu-Gly-Leu-(SEQ ID NO: 2).

26. A method according to claim 22, wherein "-peptide-" is a tetrapeptide.

27. A method according to the claim 26, wherein the tetrapeptide is -Leu-Ala-Leu-Ala-(SEQ ID NO: 1).

28. A method according to claim 22, wherein said haloacetyihydrazide is obtained by a process comprising:
  reacting a hydrazide having the formula:

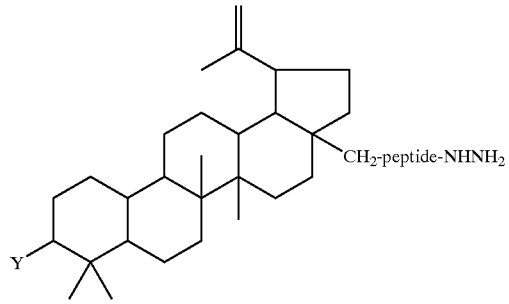

with a para-nitrophenyl α-haloacetate for a time and under conditions effective to produce the haloacetyihydrazide, and
  isolating the haloacetyihydrazide.

29. A method according to claim 28, wherein said hydrazide is obtained by a process comprising:
  reacting a betulinol peptide having the formula:

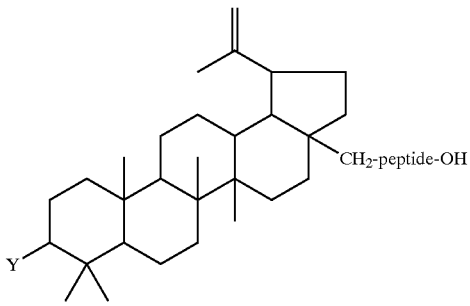

with hydrazine hydrate for a time and under conditions effective to produce the hydrazide, and
  isolating the hydrazide.

30. A method according to claim 29, wherein said betulinol peptide is obtained by a process comprising:
  reacting a compound having the formula:

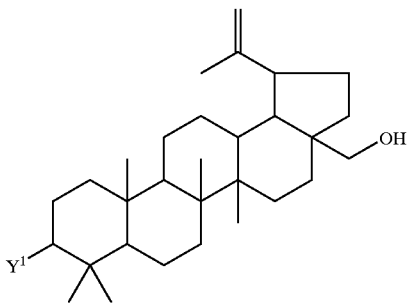

with a peptide having the formula H-peptide-OH for a time and under conditions effective to produce the betulinol peptide, and
  isolating the betulinol peptide.

31. A betulinol-antibody conjugate having the formula:

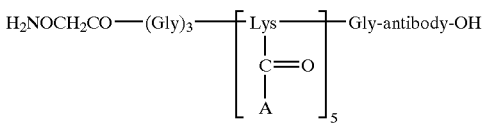

wherein
  each "A" moiety is independently selected from the group consisting of a —CHO group and a moiety having the formula:

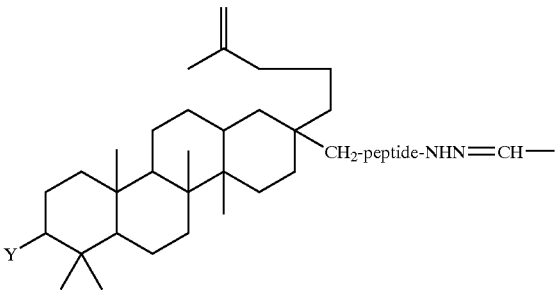

provided that at least one of A is not —CHO; and

Y is a hydroxy group, an alkoxy group, or an alkanoyloxy group.

32. A method of producing a betulinol-antibody conjugate having the formula:

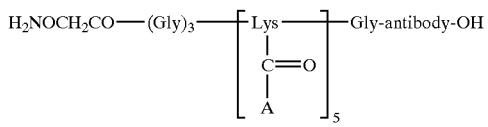

wherein
each "A" moiety is independently selected from the group consisting of a —CHO group and a moiety having the formula:

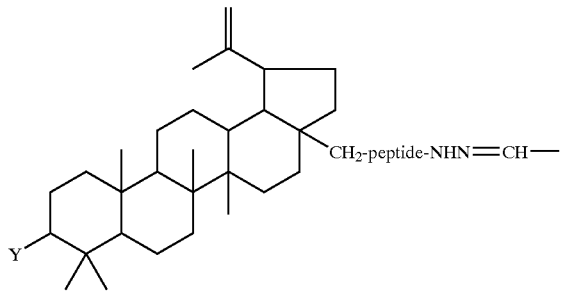

provided that at least one of A is not —CHO; and
Y is a hydroxy group, an alkoxy group, or an alkanoyloxy group, said method comprising:

reacting a carrier molecule having the formula:

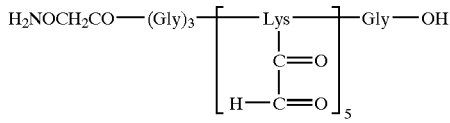

a hydrazide having the formula:

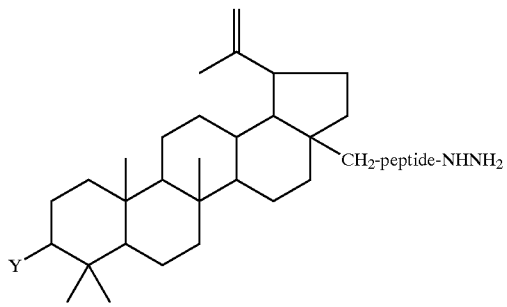

and an antibody having the formula H-antibody-OH for a time and under conditions effective to produce the betulinol-antibody conjugate, and isolating the betulinol-antibody conjugate.

33. A method of producing a betulinol-antibody conjugate having the formula:

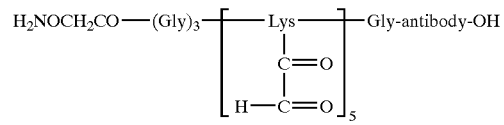

wherein
each "A" moiety is independently selected from the group consisting of a —CHO group and a moiety having the formula:

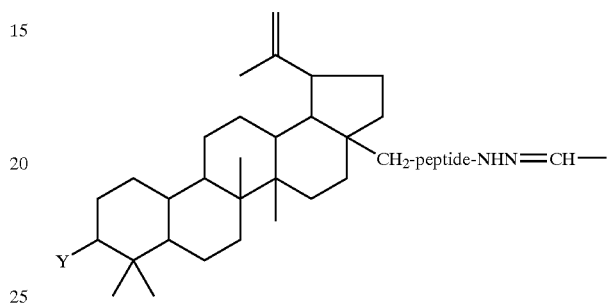

provided that at least one of A is not —CHO; and
Y is a hydroxy group, an alkoxy group, or an alkanoyloxy group, said method comprising:
reacting a carrier molecule having the formula:

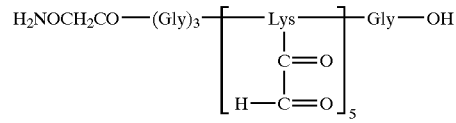

with an antibody having the formula H-antibody-OH for a time and under conditions effective to produce an antibody-bound carrier molecule having the formula:

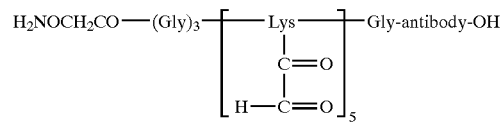

and
reacting the antibody-bound carrier molecule with a hydrazide having the formula:

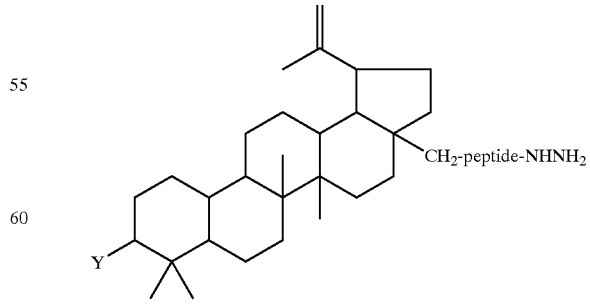

for a time and under conditions effective to produce the betulinol-antibody conjugate, and
isolating the betulinol-antibody conjugate.

34. A method of producing a betulinol-antibody conjugate having the formula:

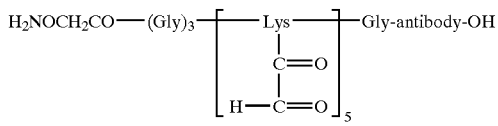

wherein
each "A" moiety is independently selected from the group consisting of a —CHO group and a moiety having the formula:

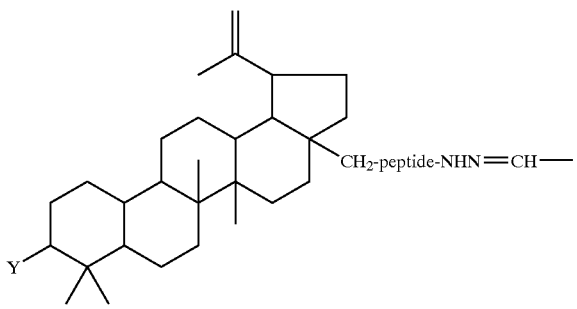

provided that at least one of A is not —CHO; and
Y is a hydroxy group, an alkoxy group, or an alkanoyloxy group,
said method comprising:
reacting a carrier molecule having the formula:

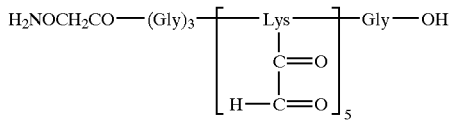

with a hydrazide having the formula:

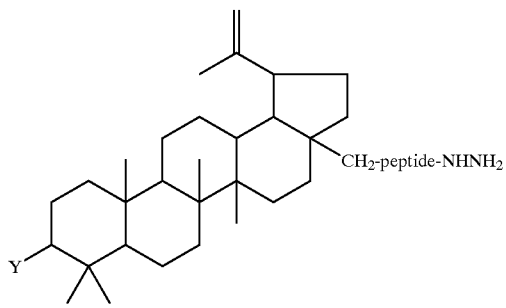

for a time and under conditions effective to produce a betulinol-bound carrier molecule having the formula:

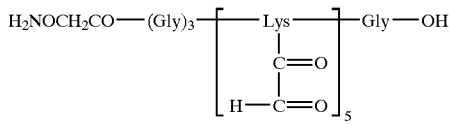

wherein at least one A is a moiety having the formula:

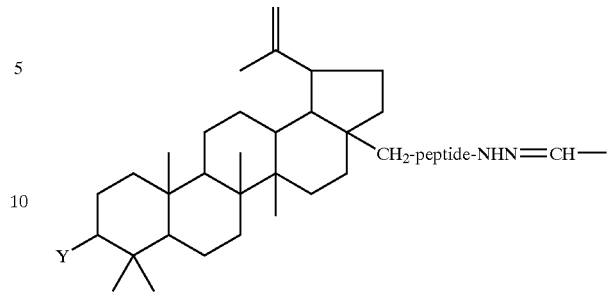

and
reacting the betulinol-bound carrier molecule with an antibody having the formula H-antibody-OH for a time and under conditions effective to produce the betulinol-antibody conjugate, and
isolating the betulinol-antibody conjugate.

35. A betulinol-antibody conjugate having the formula:

HO-antibody-spacer-(A)$_n$ wherein
A is a moiety having the formula:

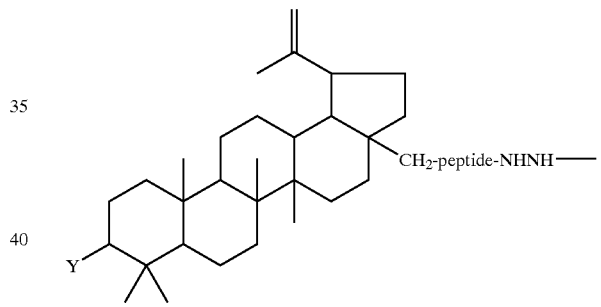

Y is a hydroxy group, an alkoxy group, or an alkanoyloxy group;
"spacer" is multivalent moiety bonded to the antibody and (A)$_n$; and
n is an integer from 1 to 100.

36. A betulinol-antibody conjugate according to claim 35, wherein -spacer-(A)$_n$ has the formula:

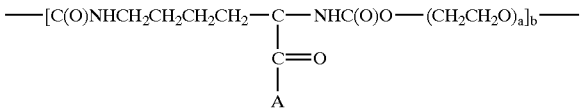

wherein
a is an integer from 1 to 100 and
b is an integer equal to n.

37. A betulinol-antibody conjugate according to claim 35, wherein "spacer" is a multivalent moiety produced from a diamine derivative of polyethylene glycol having 2-(pyridyldithio)-propionyl and N-hydroxysuccinimide ester groups bonded thereto.

38. A betulinol-antibody conjugate according to claim 35, wherein "spacer" is a multivalent moiety produced from a branched form of polyethylene glycol propionic acid N-hydroxysuccinimide ester.

39. A betulinol-antibody conjugate according to claim 38, wherein the branched form of polyethylene glycol propionic acid N-hydroxysuccinimide ester is a monomethoxypoly (ethylene glycol)-propionic acid N-hydroxysuccinimide ester.

40. A method of producing a betulinol-antibody conjugate having the formula:

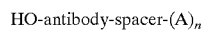

HO-antibody-spacer-(A)$_n$ wherein
A is a moiety having the formula:

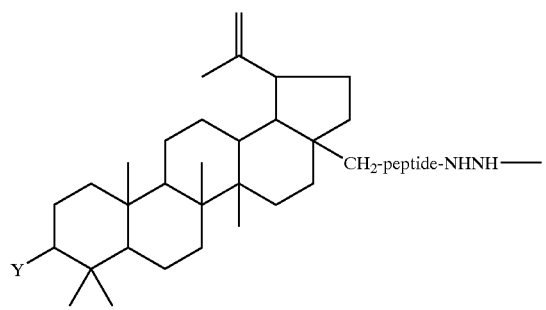

Y is a hydroxy group, an alkoxy group, or an alkanoyloxy group;
"spacer" is multivalent moiety bonded to the antibody and (A)$_n$; and
n is an integer from 1 to 100, said method comprising:

providing a "spacer" having a first reactive terminus and one or more second reactive termini;

reacting an antibody with the first reactive terminus;

reacting a hydrazide having the formula:

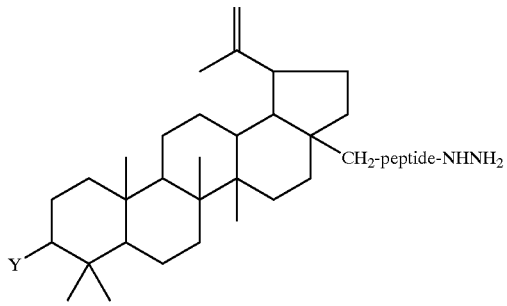

with one or more of the one or more second reactive termini for a time and under conditions effective to produce the betulinol-antibody conjugate; and
isolating the betulinol-antibody conjugate.

41. A method according to claim 40, wherein the first reactive terminus is selected from the group consisting of a hydroxy group, an aldehyde group, and a carboxyl group.

42. A method according to claim 40, wherein each of the one or more second reactive termini are independently selected from the group consisting of a hydroxy group, an aldehyde group, and a carboxyl group.

43. A method according to claim 40, wherein -spacer-(A)$_n$ has the formula:

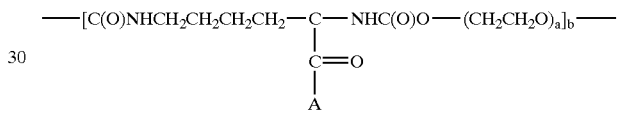

wherein
a is an integer from 1 to 100 and
b is an integer equal to n.

44. A method according to claim 40, wherein "spacer" is a multivalent moiety produced from a diamine derivative of polyethylene glycol having 2-(pyridyldithio)-propionyl and N-hydroxysuccinimide ester groups bonded thereto.

45. A method according to claim 40, wherein "spacer" is a multivalent moiety produced from a branched form of polyethylene glycol propionic acid N-hydroxysuccinimide ester.

46. A method according to claim 45, wherein the branched form of polyethylene glycol propionic acid N-hydroxysuccinimide ester is a monomethoxypoly (ethylene glycol)-propionic acid N-hydroxysuccinimide ester.

* * * * *

UNITED STATES PATENT AND TRADEMARK OFFICE
CERTIFICATE OF CORRECTION

PATENT NO. : 6,890,533 B2  Page 1 of 8
APPLICATION NO. : 09/089894
DATED : May 10, 2005
INVENTOR(S) : Arkadiy Bomshteyn, Premila Rathnam and Brij B. Saxena It is certified that error appears in the above-identified patent and that said Letters Patent is hereby corrected as shown below:

Title page,
Item [57], ABSTRACT,
Line 3, the chemical formula should appear as follows:

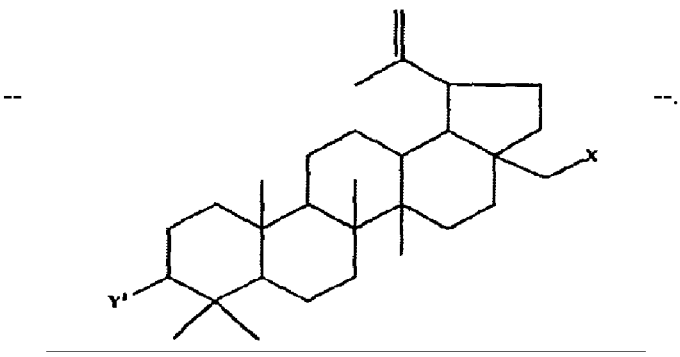

Column 2,
Lines 12-22, the chemical formula should appear as follows:

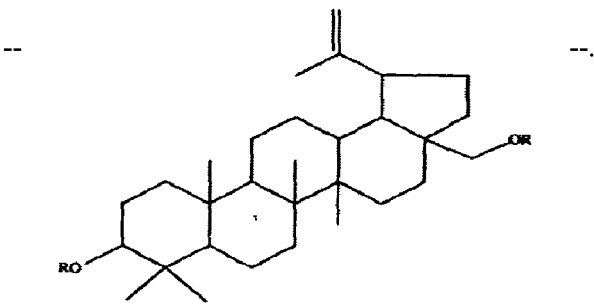

Lines 29-39, the chemical formula should appear as follows:

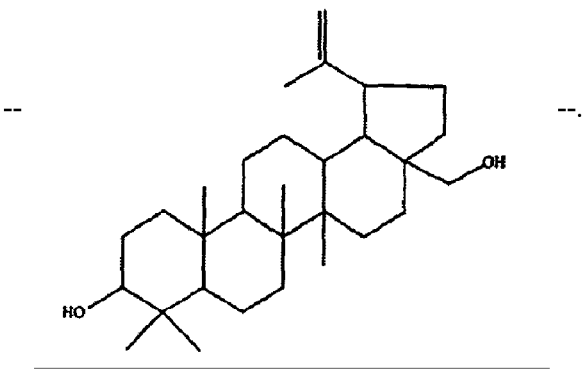

UNITED STATES PATENT AND TRADEMARK OFFICE
CERTIFICATE OF CORRECTION

PATENT NO.         : 6,890,533 B2
APPLICATION NO.    : 09/089894
DATED              : May 10, 2005
INVENTOR(S)        : Arkadiy Bomshteyn, Premila Rathnam and Brij B. Saxena It is certified that error appears in the above-identified patent and that said Letters Patent is hereby corrected as shown below:

Column 2 (cont'd),
Lines 52-62, the chemical formula should appear as follows:

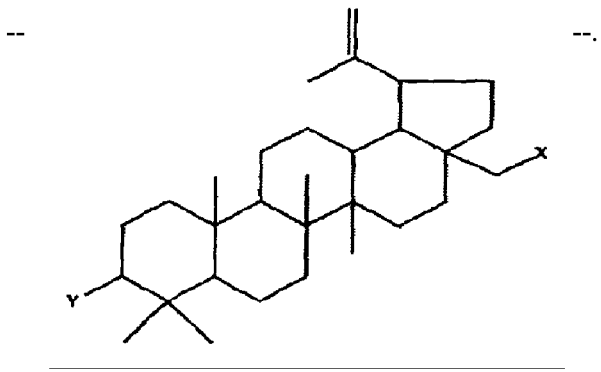

Column 7,
Lines 24-34, the chemical formula should appear as follows:

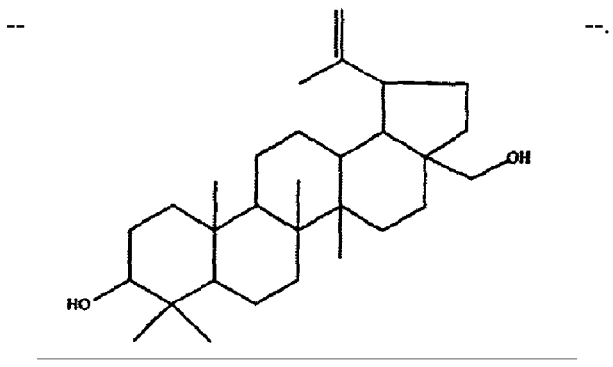

Column 9,
Lines 25-36, the chemical formula should appear as follows:

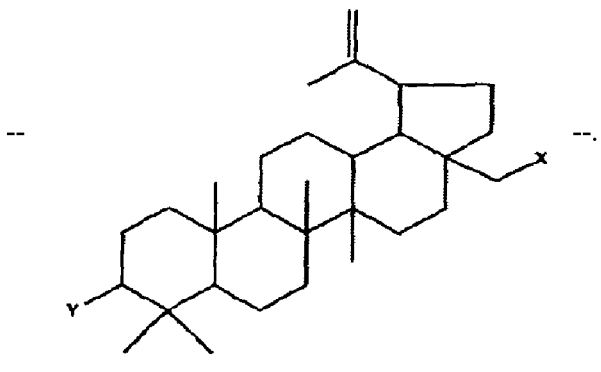

UNITED STATES PATENT AND TRADEMARK OFFICE
CERTIFICATE OF CORRECTION

PATENT NO. : 6,890,533 B2
APPLICATION NO. : 09/089894
DATED : May 10, 2005
INVENTOR(S) : Arkadiy Bomshteyn, Premila Rathnam and Brij B. Saxena It is certified that error appears in the above-identified patent and that said Letters Patent is hereby corrected as shown below:

Column 13,
Lines 19-29, the chemical formula should appear as follows:

-- 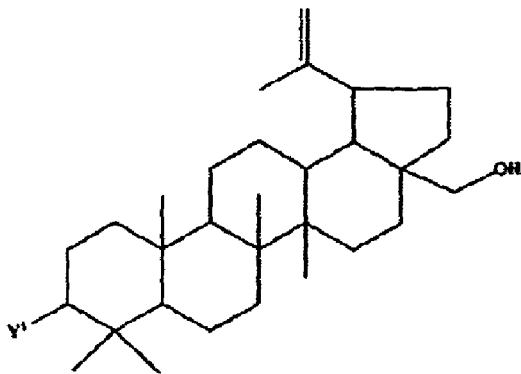 --.

Column 14,
Lines 49-60, the chemical formula should appear as follows:

-- 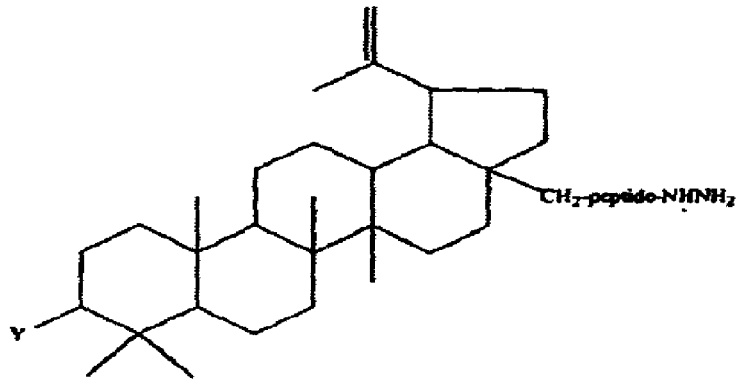 --.

Column 18,
Lines 57-60, the chemical formula should appear as follows:

-- 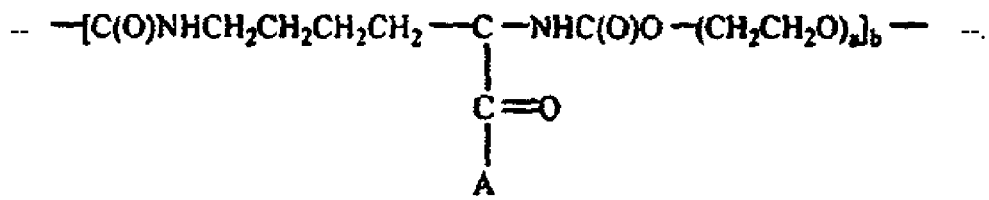 --.

UNITED STATES PATENT AND TRADEMARK OFFICE
CERTIFICATE OF CORRECTION

PATENT NO. : 6,890,533 B2
APPLICATION NO. : 09/089894
DATED : May 10, 2005
INVENTOR(S) : Arkadiy Bomshteyn, Premila Rathnam and Brij B. Saxena It is certified that error appears in the above-identified patent and that said Letters Patent is hereby corrected as shown below:

Column 19,
Lines 51-55, the chemical formula should appear as follows:

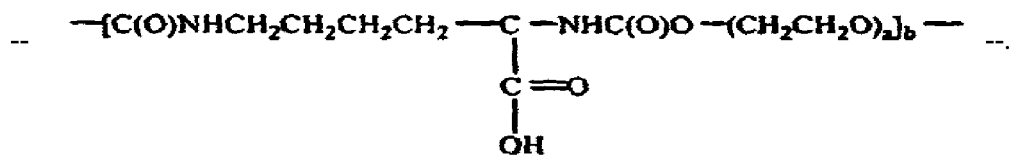

Column 21,
Lines 4-14, the chemical formula should appear as follows:

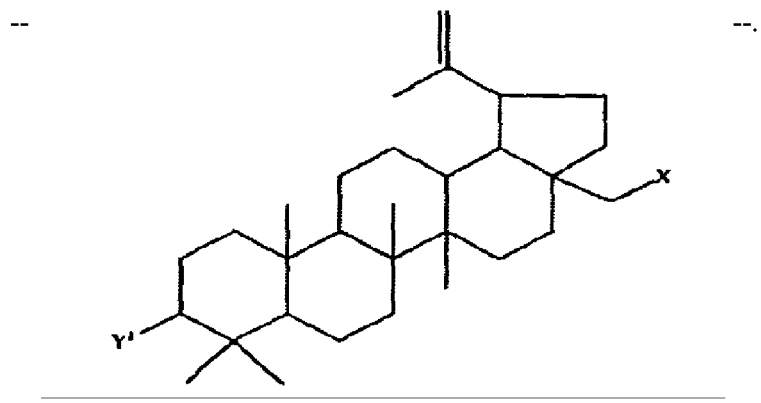

Column 29,
Lines 38-48 and 54-64, the chemical formula should appear as follows:

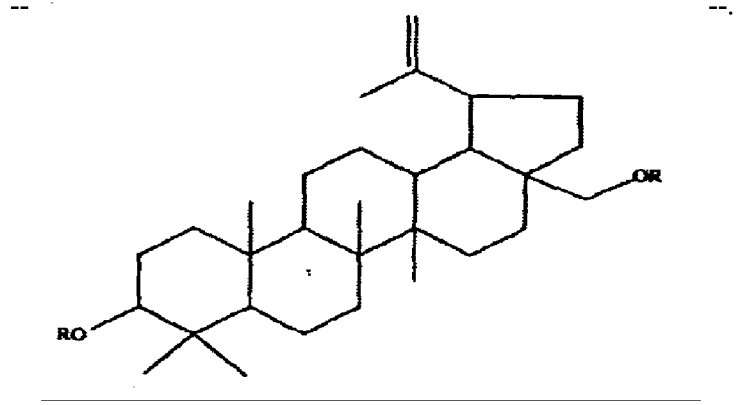

UNITED STATES PATENT AND TRADEMARK OFFICE
CERTIFICATE OF CORRECTION

PATENT NO. : 6,890,533 B2
APPLICATION NO. : 09/089894
DATED : May 10, 2005
INVENTOR(S) : Arkadiy Bomshteyn, Premila Rathnam and Brij B. Saxena It is certified that error appears in the above-identified patent and that said Letters Patent is hereby corrected as shown below:

Column 30,
Lines 38-48, the chemical formula should appear as follows:

-- 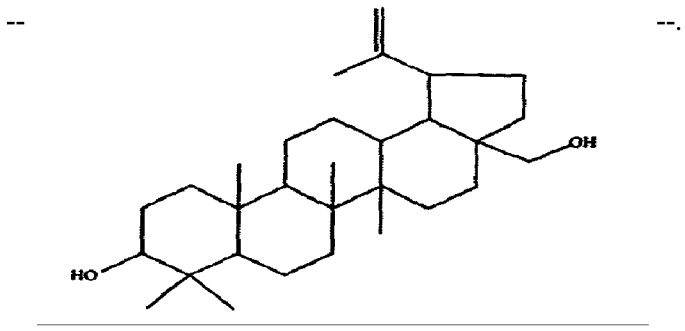 --.

Column 31,
Lines 35-46, the chemical formula should appear as follows:

-- 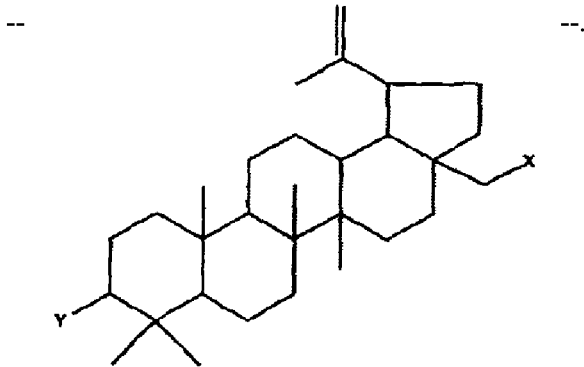 --.

Column 32,
Lines 51-62, the chemical formula should appear as follows:

-- 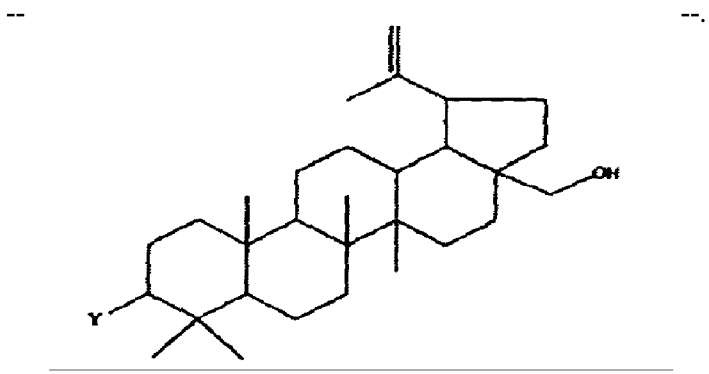 --.

UNITED STATES PATENT AND TRADEMARK OFFICE
CERTIFICATE OF CORRECTION

PATENT NO. : 6,890,533 B2
APPLICATION NO. : 09/089894
DATED : May 10, 2005
INVENTOR(S) : Arkadiy Bomshteyn, Premila Rathnam and Brij B. Saxena It is certified that error appears in the above-identified patent and that said Letters Patent is hereby corrected as shown below:

Column 33,
Lines 19, 47-48, 65 and 66, "haloacetyihydrazide" should be -- haloacetylhydrazide. --.
Line 45, "to the claim 26" should be -- to claim 26. --.
Lines 52-62, the chemical formula should appear as follows:

-- 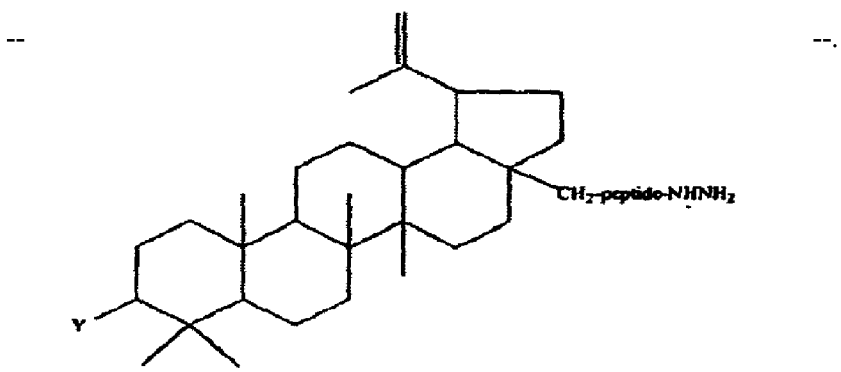 --.

Column 34,
Lines 25-36, the chemical formula should appear as follows:

-- 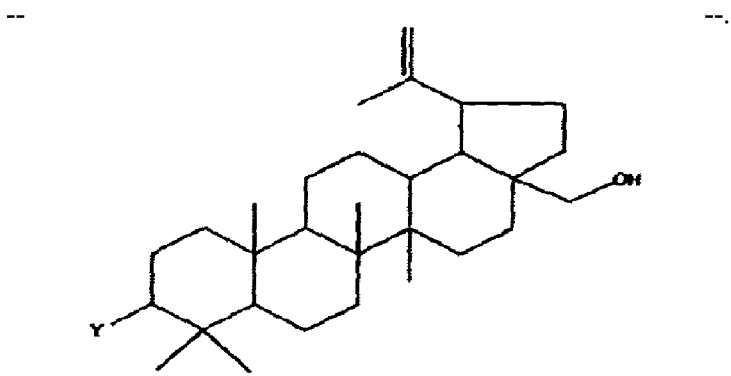 --.

UNITED STATES PATENT AND TRADEMARK OFFICE
CERTIFICATE OF CORRECTION

PATENT NO.        : 6,890,533 B2
APPLICATION NO.   : 09/089894
DATED             : May 10, 2005
INVENTOR(S)       : Arkadiy Bomshteyn, Premila Rathnam and Brij B. Saxena It is certified that error appears in the above-identified patent and that said Letters Patent is hereby corrected as shown below:

Column 35,
Lines 49-59, the chemical formula should appear as follows:

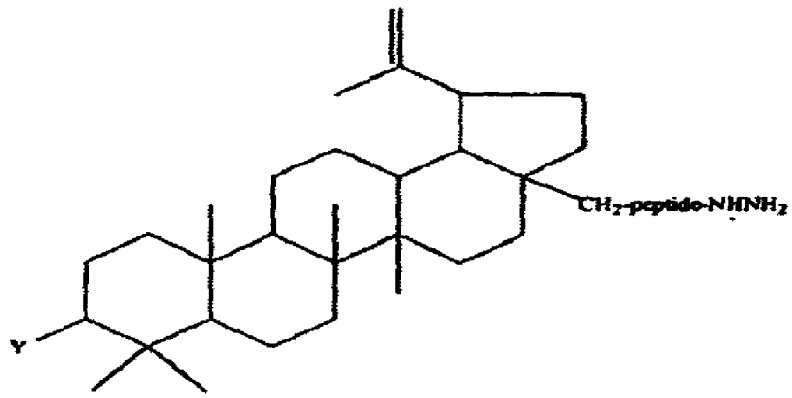

Column 36,
Lines 4-7, the chemical formula should appear as follows:

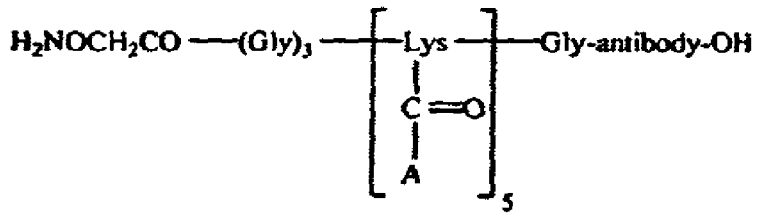

Lines 53-63, the chemical formula should appear as follows:

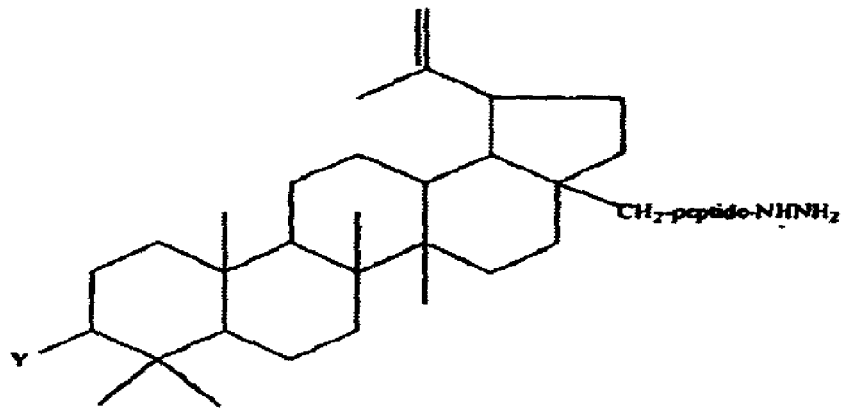

UNITED STATES PATENT AND TRADEMARK OFFICE
CERTIFICATE OF CORRECTION

PATENT NO. : 6,890,533 B2
APPLICATION NO. : 09/089894
DATED : May 10, 2005
INVENTOR(S) : Arkadiy Bomshteyn, Premila Rathnam and Brij B. Saxena It is certified that error appears in the above-identified patent and that said Letters Patent is hereby corrected as shown below:

Column 37,
Lines 4-7, the chemical formula should appear as follows:

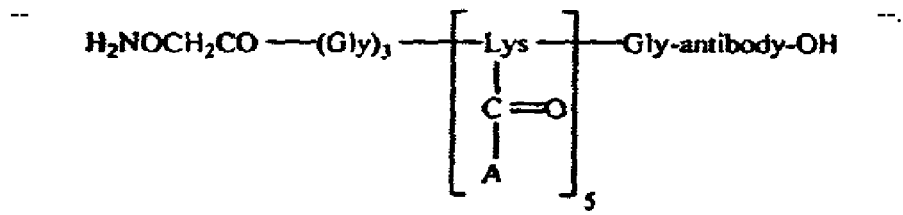

Lines 61-64, the chemical formula should appear as follows:

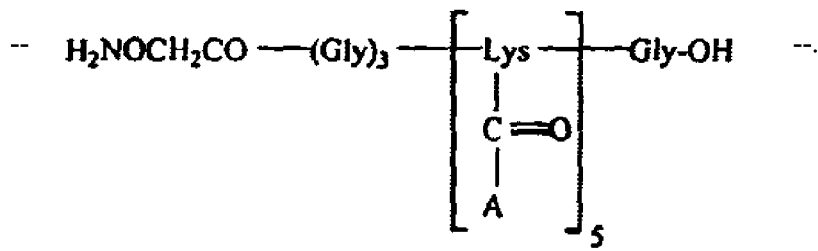

Signed and Sealed this

Twentieth Day of June, 2006

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  Carrier
      molecule

<400> SEQUENCE: 1

Leu Ala Leu Ala
  1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:  Carrier
      molecule

<400> SEQUENCE: 2

Gly Ala Leu Gly Leu
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Nonapeptide
<221> NAME/KEY: UNSURE
<222> LOCATION: (1)
<223> OTHER INFORMATION: Xaa in position 1 is Fmoc-Gly
<221> NAME/KEY: UNSURE
<222> LOCATION: (4)..(8)
<223> OTHER INFORMATION: Xaa in positions 4, 5, 6, 7, and 8 is
      Lys(t-Boc)
<221> NAME/KEY: UNSURE
<222> LOCATION: (9)
<223> OTHER INFORMATION: Xaa in position 9 is Gly-OCH2-PAM
<221> NAME/KEY: UNSURE
<222> LOCATION: (9)

<400> SEQUENCE: 3

Xaa Gly Gly Xaa Xaa Xaa Xaa Xaa Xaa
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Nonapeptide
<221> NAME/KEY: UNSURE
<222> LOCATION: (1)
```

-continued

```
<223> OTHER INFORMATION: Xaa in position 1 is Fmoc-Gly
<221> NAME/KEY: UNSURE
<222> LOCATION: (4)..(8)
<223> OTHER INFORMATION: Xaa in positions 4, 5, 6, 7, and 8 is Lys
      (t-Boc-Ser(Bzl))
<221> NAME/KEY: UNSURE
<222> LOCATION: (9)
<223> OTHER INFORMATION: Xaa in position 9 is Gly-OCH2-PAM

<400> SEQUENCE: 4

Xaa Gly Gly Xaa Xaa Xaa Xaa Xaa Xaa
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Nonapeptide
<221> NAME/KEY: UNSURE
<222> LOCATION: (1)
<223> OTHER INFORMATION: Xaa in position 1 is t-Boc-NHOCH2CO-Gly
<221> NAME/KEY: UNSURE
<222> LOCATION: (4)..(8)
<223> OTHER INFORMATION: Xaa in positions 4, 5, 6, 7, and 8 is Lys
      (t-Boc-Ser(Bzl))
<221> NAME/KEY: UNSURE
<222> LOCATION: (9)
<223> OTHER INFORMATION: Xaa in position 9 is Gly-OCH2-PAM

<400> SEQUENCE: 5

Xaa Gly Gly Xaa Xaa Xaa Xaa Xaa Xaa
  1               5
```